(12) United States Patent
Younge et al.

(10) Patent No.: US 8,388,538 B2
(45) Date of Patent: *Mar. 5, 2013

(54) SYSTEM AND METHOD FOR 3-D IMAGING

(75) Inventors: Robert G. Younge, Portola Valley, CA (US); Daniel T. Wallace, Burlingame, CA (US)

(73) Assignee: Hansen Medical, Inc., Mountain View, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/073,527

(22) Filed: Mar. 28, 2011

(65) Prior Publication Data

US 2011/0172535 A1 Jul. 14, 2011

Related U.S. Application Data

(63) Continuation of application No. 12/577,086, filed on Oct. 9, 2009, now Pat. No. 7,935,059, which is a continuation of application No. 10/923,660, filed on Aug. 20, 2004, now Pat. No. 7,618,371.

(60) Provisional application No. 60/496,944, filed on Aug. 20, 2003, provisional application No. 60/506,231, filed on Sep. 25, 2003.

(51) Int. Cl.
*A61B 8/00* (2006.01)

(52) U.S. Cl. ........................ 600/443; 345/156

(58) Field of Classification Search .................. 600/443; 345/156–184
See application file for complete search history.

(56) References Cited

U.S. PATENT DOCUMENTS

| | | | |
|---|---|---|---|
| 5,159,931 A | 11/1992 | Pini | |
| 5,181,514 A | 1/1993 | Solomon et al. | |
| 5,932,035 A | 8/1999 | Koger et al. | |
| 6,162,179 A | 12/2000 | Moore | |
| 6,398,731 B1 | 6/2002 | Mumm et al. | |
| 6,923,768 B2 | 8/2005 | Camus et al. | |
| 7,618,371 B2 | 11/2009 | Younge et al. | |
| 7,935,059 B2 | 5/2011 | Younge et al. | |
| 2002/0049375 A1 | 4/2002 | Strommer et al. | |
| 2002/0165448 A1 | 11/2002 | Ben-Haim et al. | |
| 2003/0093067 A1 | 5/2003 | Panescu | |
| 2005/0137478 A1 | 6/2005 | Younge et al. | |
| 2010/0094125 A1 | 4/2010 | Younge et al. | |

FOREIGN PATENT DOCUMENTS

| | | |
|---|---|---|
| EP | 0514584 | 11/1992 |
| WO | WO 2005/018459 | 3/2005 |

OTHER PUBLICATIONS

PCT Patent Application No. PCT/US2004/027179 filed Aug. 20, 2004 in the name of Younge et al., Search Report and Written Opinion mailed Nov. 9, 2004.
U.S. Appl. No. 10/923,660, filed Aug. 20, 2004 in the name of Young et al., non-final Office Action mailed Mar. 20, 2008.
U.S. Appl. No, 10/923,660, filed Aug. 20, 2004 in the name of Younge et al., Notice of Allowance mailed Jul. 9, 2009.
U.S. Appl. No. 12/577,086, filed Oct. 9, 2009 in the name Younge et al., non-final Office Action mailed Jun. 11, 2010.
U.S. Appl. No. 12/577,086, filed Oct. 9, 2009 in the name of Younge et al., Notice of Allowance mailed Dec. 23, 2010,.

*Primary Examiner* — Brian Casler
*Assistant Examiner* — Saurel J Selkin
(74) *Attorney, Agent, or Firm* — Levine Bagade Han LLP

(57) ABSTRACT

A system and method for recording and depicting ultrasound images of a moving object are disclosed. In a preferred embodiment, ultrasound images are acquired as the field of view of an ultrasound probe is advanced across the tissues of interest during a resting period between periods of relatively large-scale heart cycle motion. A series of images acquired during a particular resting period may be represented as a three-dimensional volume image, and the comparison of volume images from adjacent cardiac resting periods enables three-dimensional volume image modulation analysis which may be presented for a user as a moving volume image of the objects of interest within the field of view.

33 Claims, 22 Drawing Sheets

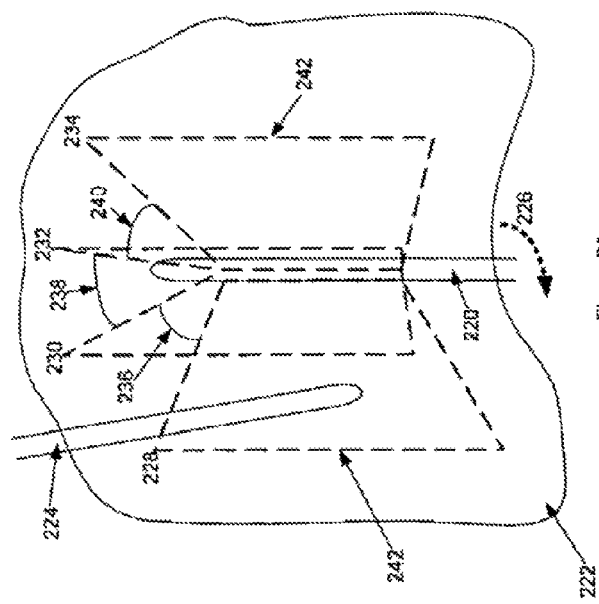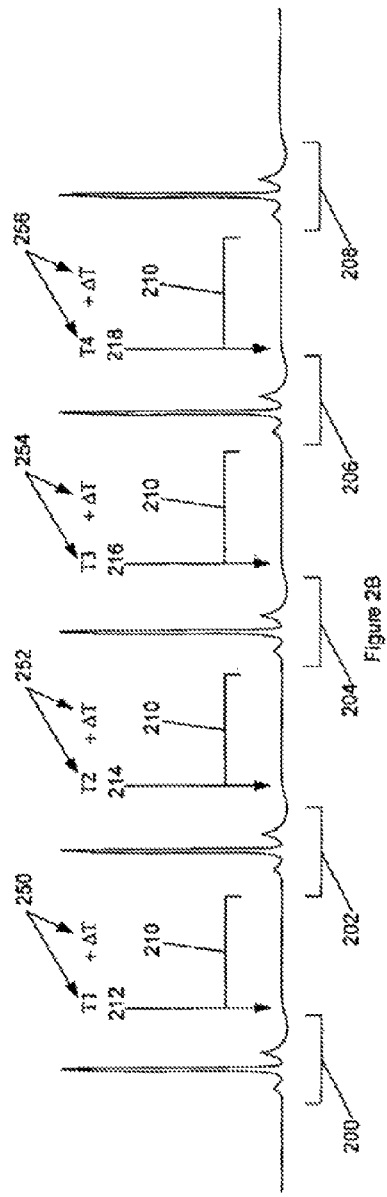

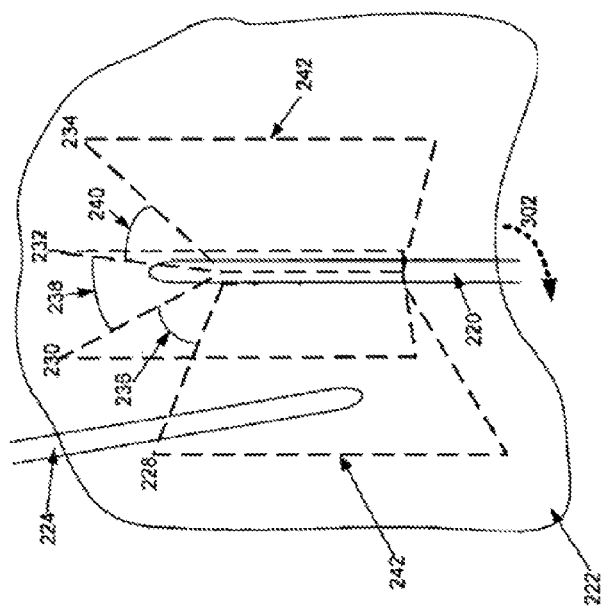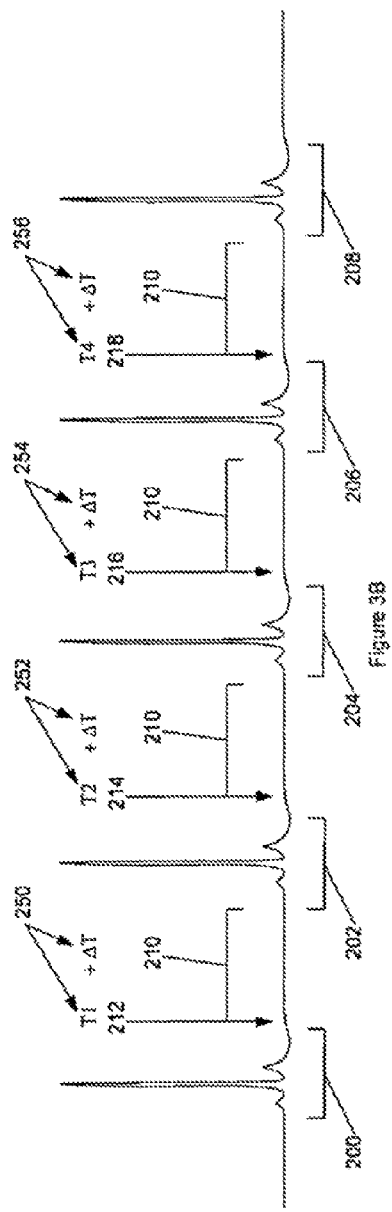

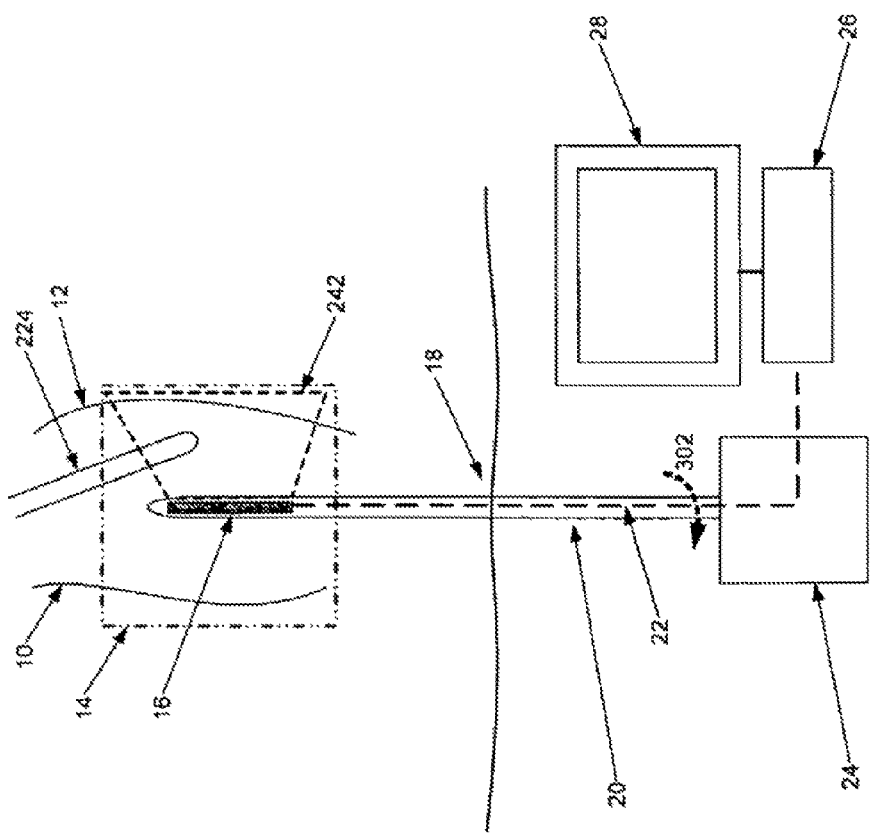

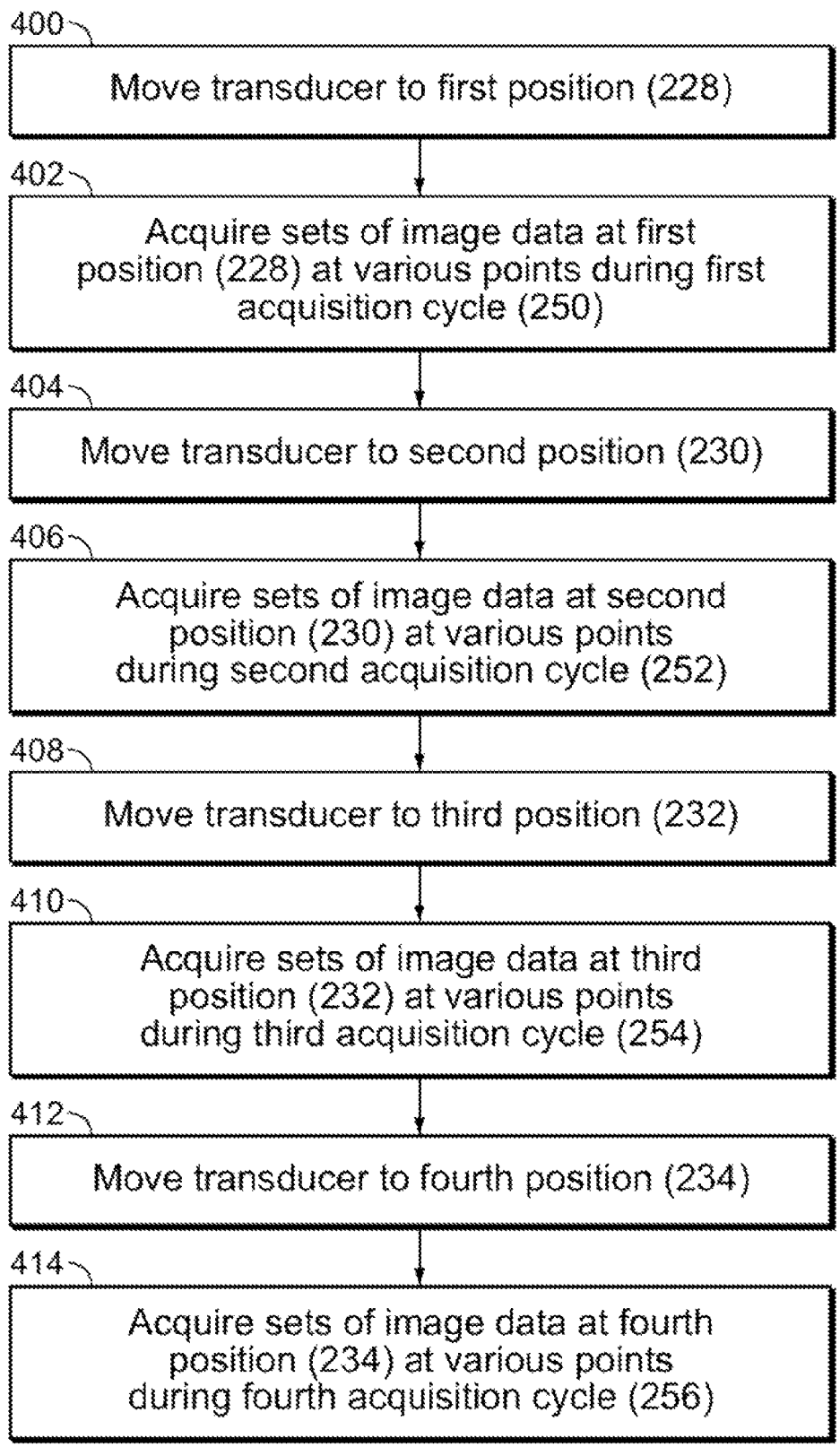
Figure 5A - *Prior Art*

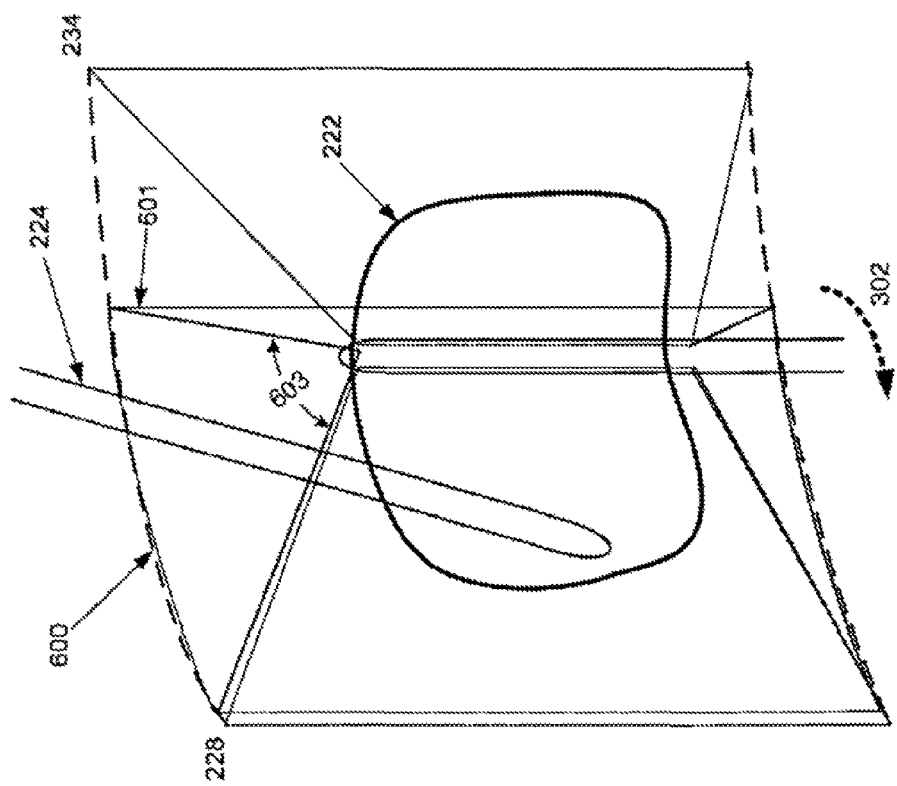

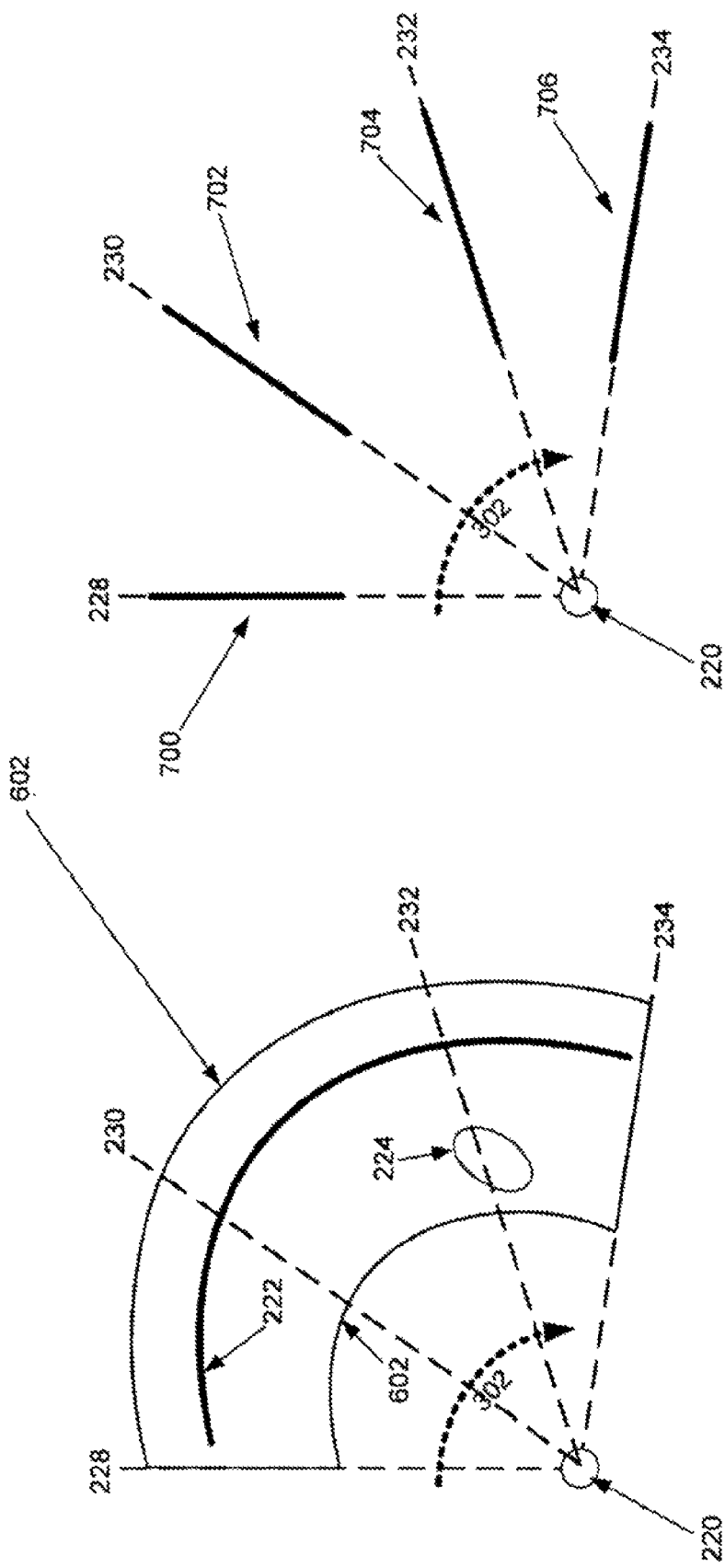

SYSTEM AND METHOD FOR 3-D IMAGING

CROSS-REFERENCE TO RELATED APPLICATIONS

This application is a continuation of U.S. patent application Ser. No. 12/577,086, filed on Oct. 9, 2009, which is a continuation of U.S. patent application Ser. No. 10/923,660, filed on Aug. 20, 2004, now U.S. Pat. No. 7,618,371, which claims priority to U.S. Provisional Patent Application Nos. 60/496,944 filed Aug. 20, 2003 and 60/506,231 filed Sep. 25, 2003, the contents of which are incorporated herein by reference in their entirety for all purposes.

BACKGROUND OF THE INVENTION

Imaging moving structures such as cardiac tissue walls and nearby medical instrumentation presents a unique set of problems not ideally addressed in three dimensions by conventional devices employing imaging modalities such as magnetic resonance imaging ("MRI"), computed tomography ("CT"), and ultrasound. One the challenges with MRI and CT imaging modalities is related to the requisite sampling rate useful for monitoring three dimensional motion of tissues moving with relatively high frequency and high amplitude motion, such as cardiac tissues. Sophisticated arrays of ultrasound transducers, available in products from suppliers such as Koninklijke Philips Electronics N.V., may be utilized to produce real-time three-dimensional visualization of relatively high-frequency, high-amplitude moving tissues such as cardiac tissues, but such devices are generally large in size and configured for transthoracic access to such tissues.

Maintaining transthoracic or similar contact and access during a procedure involving the heart below or other similarly situated tissue of the body is difficult if not impossible, depending upon the particular procedure. Smaller ultrasound systems have been designed and utilized for catheter-based deployment to provide more direct access for imaging tissues and providing instrument guidance feedback. Products such as the side-firing ultrasound catheter sold by Siemens Corporation under the tradename "AcuNav™", the diagnostic ultrasound catheters sold by EP-Technologies-Boston-Scientific Corporation under the tradename "Ultra ICE™", or the intravascular ultrasound imaging catheters sold by Jomed Corporation under the tradename "Avanar™", for example, may be combined with software and automated position advancement technology from suppliers such as TomTec Imaging Systems GmbH of Munich, Germany, to produce three-dimensional renderings of various tissue structures of the body, such as vascular and cardiac tissue structures from endovascular and endocardial perspectives. The ultrasound transducer hardware comprising such systems generally is fairly simple due to size constraints, and this simplicity is advantageous for device complexity, cost, and disposability reasons. Use of these conventional systems to produce three-dimensional renderings, however, generally requires hybridizing or "gluing together" datasets captured over relatively long periods of time employing assumptions of tissue motion cycle homogeneity to produce three-dimensional renderings.

In medical fields such as remotely actuated or minimally invasive surgery, it is desirable to have accurate, timely information regarding, the relative positioning of remotely deployed medical devices and nearby tissue structures such as tissue walls. For example, one may want to biopsy a portion of a tissue wall with a mechanical end effector, inject something into and not beyond a tissue wall, or touch a tissue wall with an electrode, and have some confirmation, preferably in three-dimensions, of the relative positioning between pertinent objects during such procedures. There remains a need for a means to produce timely three-dimensional relative positioning data utilizing a noninvasive modality such as ultrasound via relatively simple structures and techniques.

FILED OF INVENTION

The present invention relates generally to ultrasound imaging systems and, more particularly, to ultrasound imaging systems acquiring two-dimensional ultrasound images of a heart for display in a three-dimensional orientation.

BRIEF DESCRIPTION OF THE DRAWINGS

Preferred embodiments and other aspects of the present invention are illustrated in the figures of the accompanying drawings, in which like references indicate similar elements. Features shown in the drawings are not intended to be drawn to scale, nor are they intended to be shown in precise positional relationship.

FIG. 2A depicts various aspects of a conventional technique for creating a three-dimensional image of a subject tissue mass and/or medical instrument.

FIG. 2B depicts an electrocardiogram associated with the imaging technique illustrated in FIG. 2A.

FIG. 3A depicts various aspects of one embodiment of the inventive technique for creating a three-dimensional image of a subject tissue mass and/or medical instrument.

FIG. 3B depicts an electrocardiogram associated with the imaging technique illustrated in FIG. 3A.

FIG. 4A depicts various aspects of one embodiment of an imaging system in accordance with the present invention.

FIG. 5A depicts a flow chart representation of a conventional imaging technique.

FIG. 7D depicts a side view of the objects and fields of view similar to those depicted in FIG. 7C.

FIG. 8A depicts a top view of a relatively focused field of view path capturing aspects of a subject tissue mass and medical instrument.

FIG. 8B depicts a series of images that may be acquired utilizing the field of view path illustrated in FIG. 8A.

DETAILED DESCRIPTION OF THE INVENTION

In the following detailed description of embodiments of the invention, reference is made to the accompanying drawings in which like references indicate similar elements. The illustrative embodiments described herein are disclosed in sufficient detail to enable those skilled in the art to practice the invention. The following detailed description is therefore not provided, or otherwise to be taken, in a limiting sense, and the scope of the invention is defined only by the appended claims.

Figure 1:
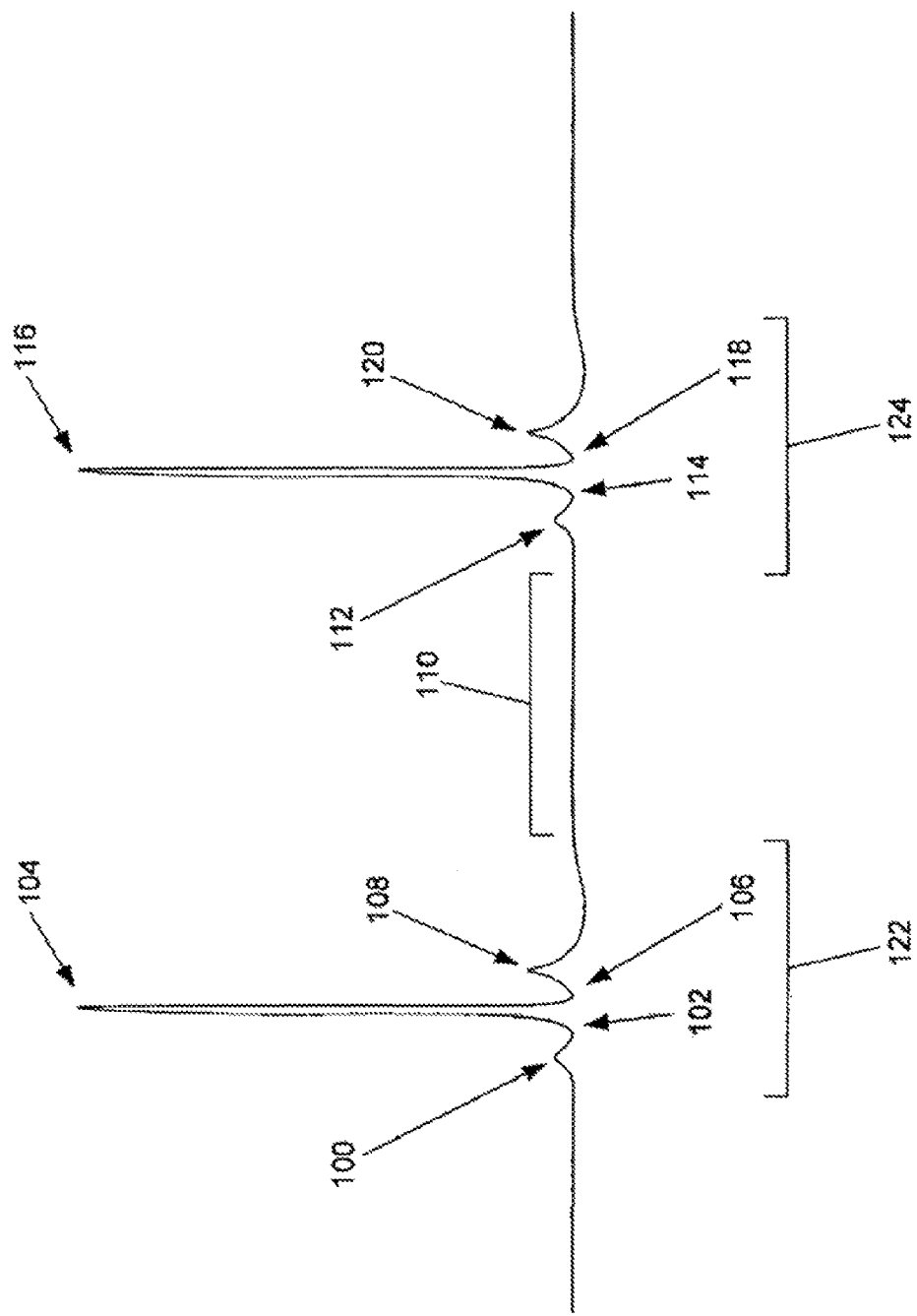
FIG. 1 depicts an electrocardiogram plot of voltage versus time for a typical human heart.

Referring to FIG. 1, an electrocardiogram ("EKG") tracing for a human heart is depicted. The two systolic heart cycles (122, 124) depicted are separated in time by a resting period (110) of relatively low heart activity, during the diastolic period of the heart cycle. Each of the active systolic heart cycles (122, 124) in a healthy patient typically comprises a P-wave (100, 112), followed by a Q-wave (102, 114), then a relatively high amplitude R-wave (104, 116), an S-wave (106, 118), and a T-wave (108, 120) before returning to the relative inactivity during a resting period (110). As discussed above, conventional ultrasound-based techniques for three-dimensional visualization may involve compiling datasets from several steps of acquiring images over time during adjacent resting periods (110) and utilizing assumptions regarding the motion of objects within the pertinent field of view during such resting periods. FIGS. 2A and 2B are useful in illustrating such convention.

Referring to FIG. 2A, a subject tissue mass (222) is positioned in actual three-dimensional space adjacent a medical instrument (224). To visualize the relative positioning of such objects, a side-firing ultrasound instrument or catheter (220) may be positioned as shown, using conventional intravascular or intralumenal delivery techniques, for example, to capture, in a series of images, a target volume of the tissue mass (222) and medical instrument (224), or portions thereof, within the field of view (242) of the ultrasound transducer. Using conventional techniques, the ultrasound field of view (242) may be oriented in a first position (228) and utilized to acquire a first series of images while in the first position (228), generally during a resting cycle between two systolic heart cycles, for example, in the case of a heart tissue subject.

Referring to FIG. 2B, this first series of images may be acquired during a first acquisition cycle (250) positioned between a first systolic heart cycle (200) and a second systolic heart cycle (202). The first acquisition cycle (250) may be defined by a first acquisition start time (212), at which the first image in the first series is acquired, and a change in time ("ΔT") during which the remainder of the images of the first series are acquired, as illustrated in FIG. 2B. For example, during the first acquisition cycle (250), four ultrasound images may be acquired with the transducer field of view in the first position (228).

Similarly, subsequent to the second systolic heart cycle (202) and a repositioning (226) of the transducer field of view (242) to a second position (230), a second series of images may be acquired during a second acquisition cycle (252) defined by a second acquisition cycle start time (214) and a "ΔT" (210) as illustrated. Further, subsequent to the third systolic heart cycle (204) and a repositioning (226) of the transducer field of view (242) to a third position (232), a third series of images may be acquired during a third acquisition cycle (254) defined by a third acquisition cycle start time (216) and a ΔT (210) as illustrated. Finally in this illustration, subsequent to the fourth systolic heart cycle (206) and a repositioning (226) of the transducer field of view (242) to a fourth position (234), a fourth series of images may be acquired during a fourth acquisition cycle (256) defined by a fourth acquisition cycle start time (218) and a ΔT (210) as illustrated. Such a pattern may be repeated past a fifth systolic heart cycle (208) as would be apparent to one skilled in the art. The incremental repositioning of the transducer field of view (242) between positions (228, 230, 232, 234) may be associated with substantially equivalent changes in rotational position (236, 238, 240) of the transducer field of view (242), as illustrated in FIG. 2A.

The scenario described above in reference to FIGS. 2A and 2B represents a fairly good case scenario utilizing conventional hardware and techniques, since many systems are incapable of repositioning between immediately adjacent acquisition cycles, and instead must consume one or more systolic heart cycles for repositioning in between systolic cycles used for acquisition. For example, a typical conventional system may acquire a series of images at the first position (228) during a first systolic cycle, then utilize the next immediately adjacent systolic cycle for repositioning to a second position (230), and resume acquiring with the second acquisition cycle during a third systolic cycle, thereby stretching out the process in time to an even greater degree than illustrated in FIG. 2B.

Figure 2C:
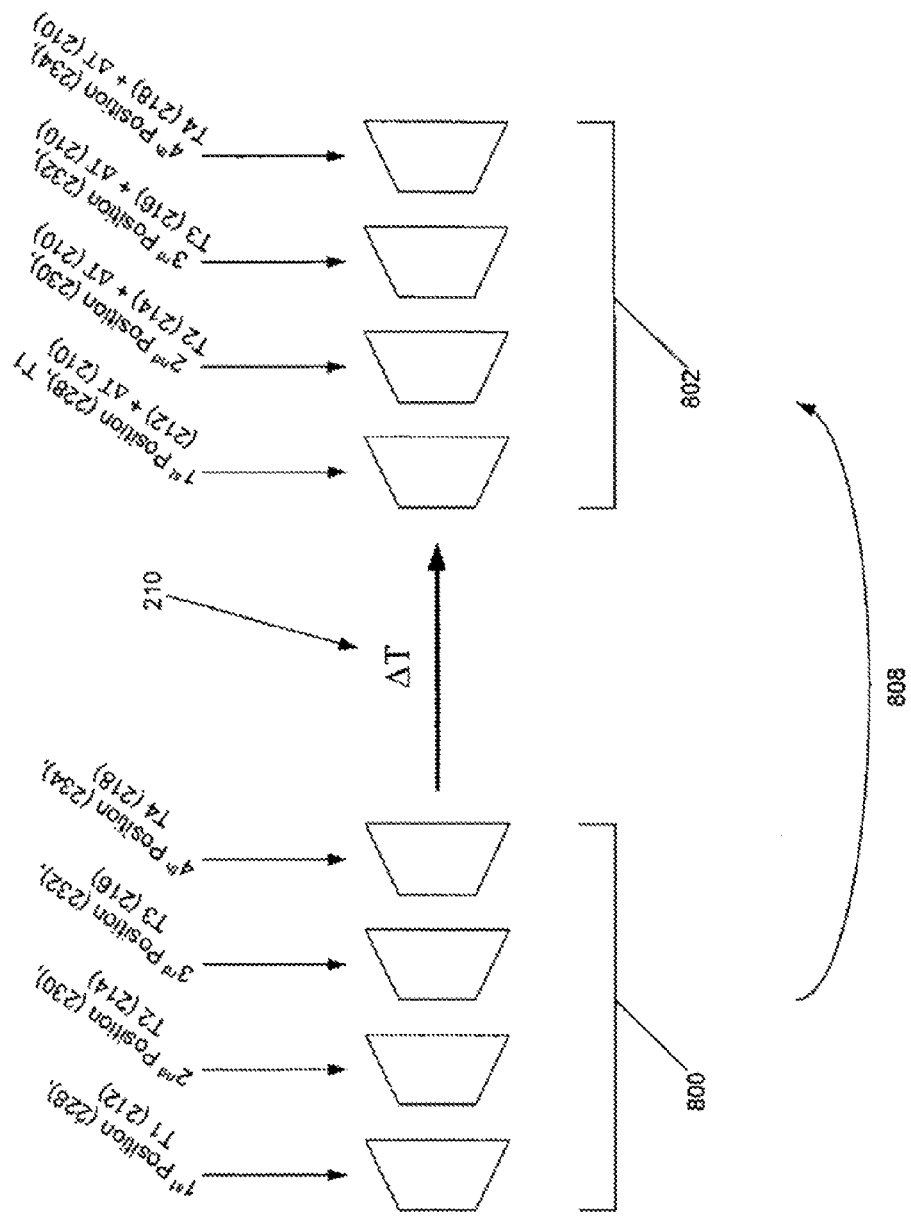
FIG. 2C depicts various aspects of a conventional technique for creating a three-dimensional image of a subject tissue mass and/or medical instrument.

Subsequent to such an image acquisition schema, data from each of the acquisition cycles (250, 252, 254, 256) may be complied into a volumetric representation of the imaged objects (222, 224) moving per the modulation of four image "slices", each of which is associated with one of the field of view positions (228, 230, 232, 234), over time. For example, to produce a visualization of the changes in relative positioning of objects (222, 224) over a time period such as ΔT, a first four-image volumetric representation comprising a first image acquired at T1 (212) and the first transducer field of view position (228), next to a second image acquired at T2 (214) and the second transducer field of view position (230), next to a third image acquired at T3 (216) and the third transducer field of view position (232), next to a fourth image acquired at T4 (218), may be compared with a second four-image volumetric representation comprising a first image acquired at T1 (212)+ΔT (210) and the first transducer field of view position (228), next to a second image acquired at T2 (214)+ΔT (210) and the second transducer field of view position (230), next to a third image acquired at T3 (216)+ΔT (210) and the third transducer field of view position (232), next to a fourth image acquired at T4 (218)+ΔT (210). The terms "volumetric image", "volumetric representation", and "image volume" are all used in reference to conventional techniques commonly used in medical imaging, for example, wherein a series of images acquired at different positions along or about a target volume are positioned adjacently within a graphical display interface, in spatial orientations relative to each other and the acquiring device similar to those during acquisition, to facilitate representation of the state of the object in three-dimensional format. One such schema is illustrated in FIG. 2C. Referring to FIG. 2C, a first image volume (800) assembled from four heart cycles is compared (808) with a second image volume (802), also assembled from four heart cycles in this example, to provide a conventional three-dimensional visualization schema which may be displayed offline in simulated real-time. With such a technique, each of the image volumes (800, 802) is utilized like a depiction of the state of the pertinent three dimensional objects at a given time, and changes in the image volume may be interpreted as changes in the relative positions of objects within the image volume over time.

One of the key challenges with such conventional schemas is accurately and repeatably gating the acquisition cycle start times T1 (212), T2 (214), T3 (216), and T4 (218) with the systolic heart cycle (200, 202, 204, 206, 208) activity. Errors are introduced into such schemas as the result of gating errors, heart cycle irregularities, and other cycles or movements, such as breathing cycles, which may not be gated with the heart cycle. As would be apparent to one skilled in the art, "gluing together" an image volume from four different heart cycles for comparison with another image volume for three-dimensional object relative position visualization inherently involves assumptions and error—and also fails to accurately represent the state of the image volume together at any given time period for visualization purposes. In other words, it is preferable to sequentially compare image volumes comprising individual images actually acquired in sequence—to accurately represent change within a given image volume over time. Conventional systems such as those described above essentially produce a three-dimensional dataset by gluing together images acquired at different times, then replay a simulated three-dimensional motion image in an offline format which is of relatively low utility as pertains to real-time device guidance or positional monitoring.

Figure 3C:
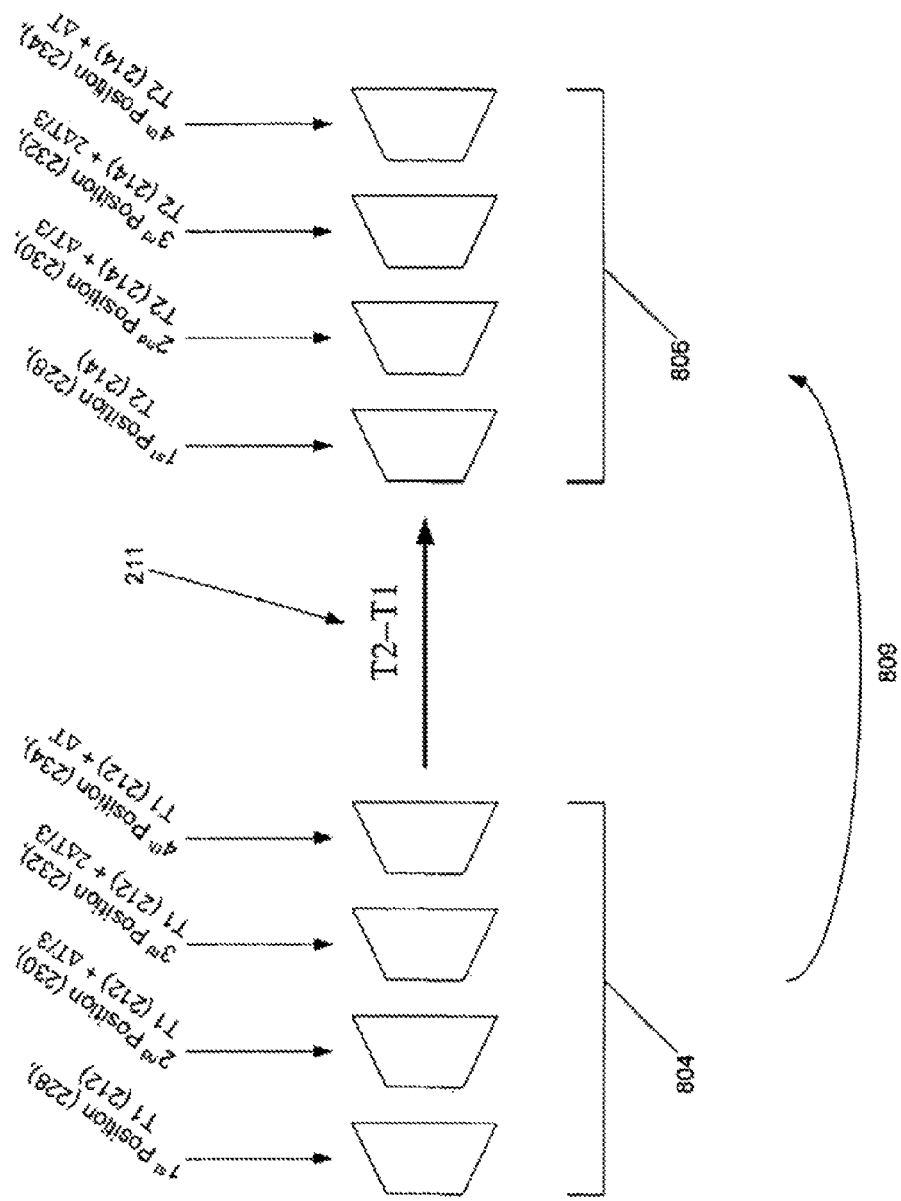
FIG. 3C depicts various aspects of one embodiment of the inventive technique for creating a three-dimensional image of a subject tissue mass and/or medical instrument.

Referring to FIGS. 3A-3C, the inventive system and technique improve upon the inherent problems with conventional techniques through sequential image acquisition and repositioning, preferably within the same resting period or adjacent resting periods, of the subject objects within a selected target volume. Referring to FIG. 3A, an embodiment analogous to that illustrated in FIG. 2A is depicted, with the exception that the embodiment of FIG. 3A is configured to change field of view position between, and in other embodiments during, acquisition of successive images. In one embodiment, for example, subsequent to acquisition of a first image at a first field of view position (228) of an ultrasound transducer coupled to a medical device instrument structure (220) such as a catheter, the field of view (242) is rotated (302) from a first field of view position (228) to a second field of view position (230), before acquisition of the next image. Such a pattern is continued with images being acquired in between repositioning movements to a third field of view position (232) and a fourth field of view position (2.34). In one embodiment, the change in rotational orientation of the transducer between each acquisition position is maintained at a substantially constant angular rotation value. In a preferred embodiment, as illustrated in FIG. 3B, four successive images are acquired at four field of view positions (228, 230, 232, 234) during multiple successive resting periods between systolic heart cycles (200, 202, 204, 206, 208). In one embodiment, it is desirable to acquire during four or more immediately successive or adjacent systolic heart cycles to facilitate observing the motion of the pertinent structures in real or near-real time on an imaging display.

Referring to FIG. 4A, one embodiment of a system for gathering, processing, and displaying three-dimensional images as described herein is depicted. In the depicted embodiment, a target volume (14) encompassing portions of two tissue walls (10, 12) and a medical instrument (224) is selected by positioning an ultrasound transducer (16) at the end of an elongate flexible member (20), such as a roughly cylindrical member or catheter, so the field of view (242) of the transducer (16) may capture the pertinent structures of interest as the elongate flexible member (20) is rotated (302). In the depicted embodiment, the elongate flexible member (20) preferably is delivered or positioned into the body (18) through an existing lumen, such as a gastrointestinal lumen, endovascular lumen, or endocardial space, for example. Ultrasound catheters have been found useful for observing tissues such as endovascular walls and endocardial walls, in part due to the access provided by catheter-based structures. In the depicted embodiment, the elongate flexible member (20) couples the ultrasound transducer (16) to a drive mechanism (24) configured to controllably reposition the ultrasound transducer (16) through rotational drive. The drive mechanism (24) preferably comprises an electric motor of the stepper or linear format, such as those known to those in the art and available from suppliers such as MicroMo Electronics, Inc. and Maxon Precision Motor, Inc. The drive mechanism (24) may also comprise a gearbox, depending upon the physical demands upon the motor, and a positional encoder, such as those available from Hewlett Packard Company, for monitoring rotational positioning of the attached elongate flexible member (20) as it is rotated (302) by the drive mechanism (24). Drive systems comprising gearboxes, motors, encoders, and coupling structures configured to interface with flexible members (20) such as the ultrasound catheter sold under the tradename AcuNav™ by Siemens Corporation are available from producers such as TomTec Imaging Systems GmbH of Germany. To prevent windup or binding of transmission lines (22) within the elongate flexible member (20) as they interface with the drive mechanism (24), conventional commutator interfaces (not shown) may be utilized, as would be apparent to one skilled in the art. Due to potential signal degeneration and noise problems associated with commutator type interfaces, in embodiments wherein the elongate flexible member (20) is repositioned before experiencing more than about 2 or 3 complete revolutions, direct leads are maintained and configured with enough slack to permit such levels of windup without functional degradation.

In the depicted embodiment, a processor (26), preferably comprising an integrated computer system, is in communication (22) with the ultrasound transducer (16) to receive and manipulate images acquired by the ultrasound transducer (16), and deliver the images to a display system (28), such as a conventional computer monitor. In one embodiment having relatively elementary controls, the drive mechanism (24) may be operated using manual controls separate from the processor (26), and the processor (26) may be configured merely to receive data signals from the ultrasound transducer (16) for displaying images with the display system (28). In other embodiments, the interaction between the processor (26) and drive mechanism preferably is more complex, utilizing conventional software-based device interaction techniques.

Figure 4B:
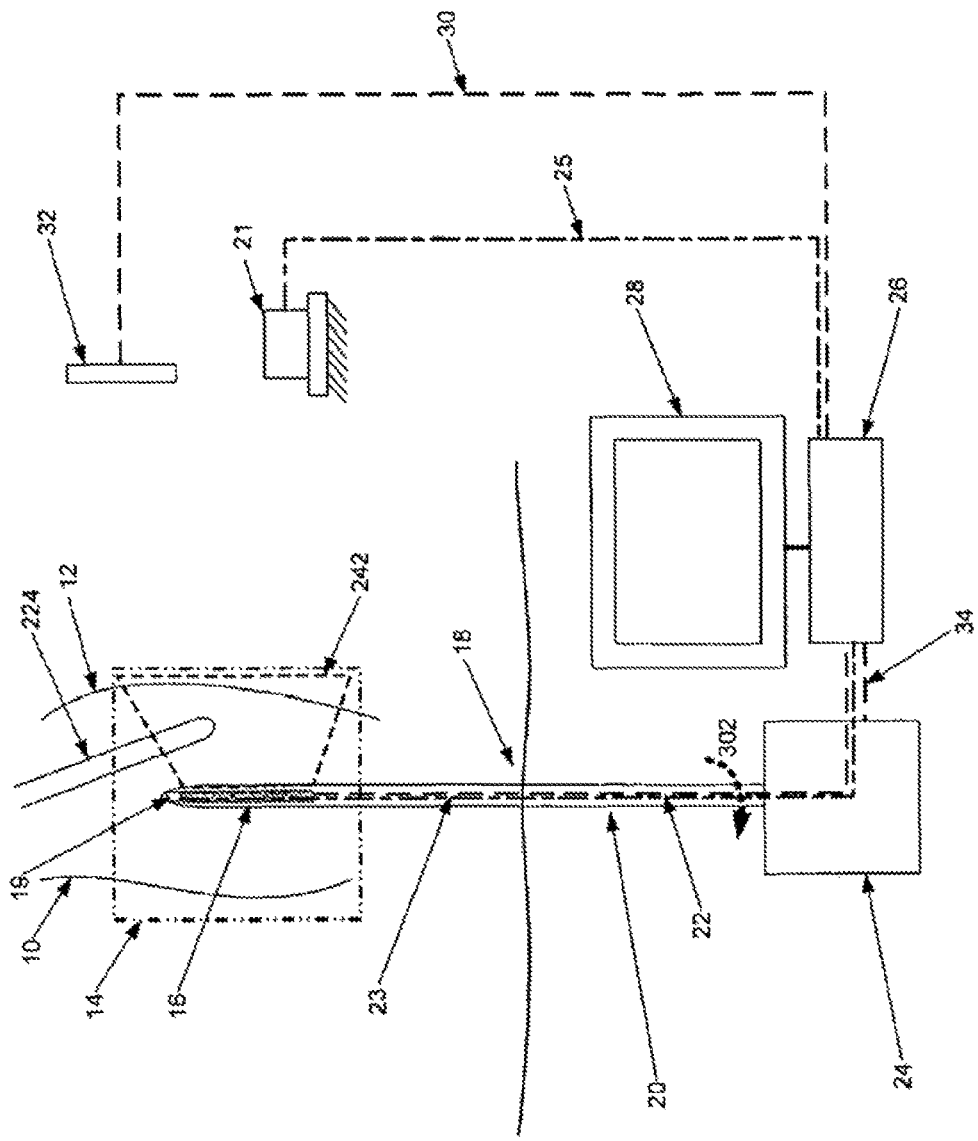
FIG. 4B depicts various aspects of one embodiment of an imaging system in accordance with the present invention.

Referring to FIG. 4B, for example, an embodiment similar to that of FIG. 4A is depicted wherein the drive mechanism (24), ultrasound transducer (16), and processor (26) have a feedback and control interaction. The embodiment depicted in FIG. 4B also comprises a biological signal sensor (32), such as an EKG sensor, which is in communication (30) with the processor (26) to facilitate image processing and drive mechanism control as related to an incoming biological signal. As would be apparent to one skilled in the art, having the system configured wherein the processor (26) receives (34) encoder data from the drive mechanism (24), receives (22) transducer data from the ultrasound transducer (16), receives (30) biological signal data from a biological signal sensor (32), sends (34) position actuation signals to the drive mechanism (24), and sends image data to a display system (28) facilitates capture, processing, and display of data as described, for example, in reference to FIGS. 3A-3C.

Referring to FIG. 4B, in another embodiment, a preferred system comprises a localization device (19) and localization module (21) configured to provide the processor (26) with three-dimensional spatial coordinate system positional data, such as X-Y-Z position of the distal portion of an ultrasound transducer (16) within a Cartesian coordinate system at the time an image in a sequence is acquired, or X-Y-X position in addition to orientation data at the time an image in a sequence is acquired, pertinent to the structure to which one or more localization devices is coupled, which may be associated with acquired image data to position and/or orient slices precisely relative to each other and correct for relative movement between an ultrasound transducer (16) and surrounding pertinent structures during an acquisition cycle outside of the expected rotational relative movement between the ultrasound transducer (16) and surrounding structures. Having position and/or orientation data acquired along with each image in a sequence provides additional data to the computer which may be utilized to orient the data, correct the data, and display the data in for example, intuitive alignment relative to other two-dimensional or three-dimensional image information, as would be apparent to one skilled in the art. In the embodiment depicted in FIG. 4C, a localization device (19) comprising three orthogonally-oriented coils is coupled to the distal tip of the instrument adjacent the transducer (16). An electrical lead (23) positioned adjacent the transducer lead (22) hardware places the localization device (19) in communication with the processor (26). The localization device (19) in the depicted embodiment preferably is partially or fully encapsulated by the distal structure material of the instrument tip, preferably utilizing a lumen sized to distally house the small, three coil localization device (19) construct, and the elongate lead (23) more proximately.

Localization devices (19), such as sets of orthogonally-oriented coils or other structures, and localization modules (21), generally mounted to a stable structure such as a table and comprising transmitters, receivers, and other components, are available as precise device localization systems from suppliers such as Medtronic Corporation, Ascension Technology Corporation, SuperDimension Ltd., and the Biosense-Webster division of Johnson & Johnson Corporation. Such systems may be configured to communicate with a processor (24) via electronic leads (23, 25), as shown in FIG. 4D, and to communicate with each other via electromagnetic radiation, in a configuration, for example, wherein a module comprises an electromagnetic field detector or transmitter, and a device coil comprises a conducting material configured to detect nearby electromagnetic fields. Other conventional localization systems utilize electrical conductivity or other forms of radiation to detect position and/or orientation of medical instruments.

Figure 4C:
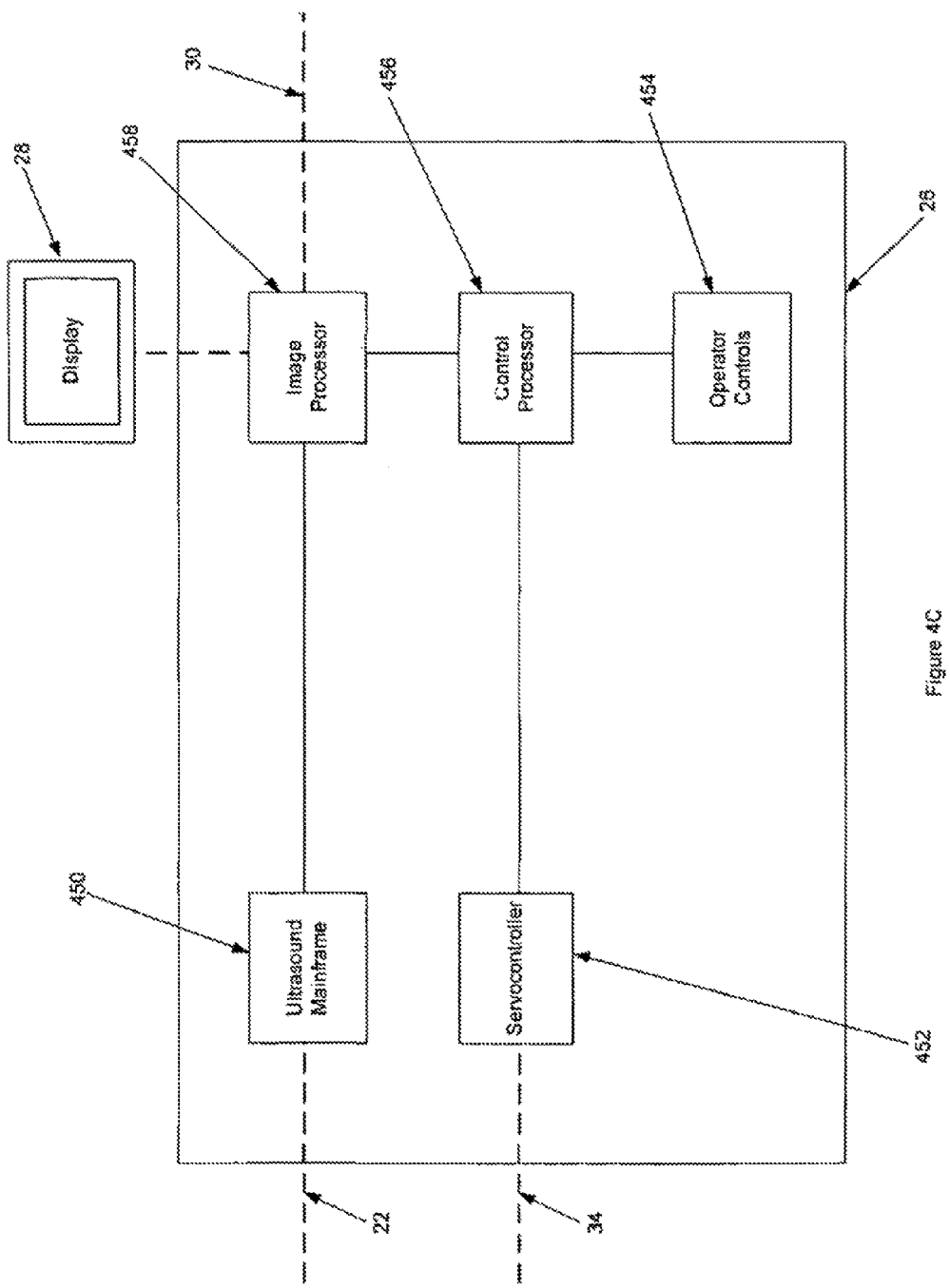
FIG. 4C depicts various aspects of one embodiment of an imaging system in accordance with the present invention.

Referring to FIG. 4C, further detail of preferred processor (26) componentry is depicted. In the depicted embodiment, the processor (26) comprises a control processor (456) in communication with a servocontroller (452), an image processor (458), and operator controls (454). The image processor (458) is in communication with an ultrasound mainframe (450) and a display system (28). In one embodiment, the control processor (456) is a conventional personal computer type microprocessor resident in a personal computer, and the servocontroller (452) comprises one or more boards for digital and analog signal input and output also resident in or coupled to the same personal computer, the control processor (456) and servocontroller (452) each being operated by software resident on the computer. Many conventional control system software and hardware packages, such as those sold under the tradename "dSPACE" by Digital Signal Processing and Control GmbH of Germany, are suitable for such an application. The operator controls (454) preferably comprise conventional devices such as a mouse, a foot pedal, or a microphone which may be utilized to communicate control inputs, such as on/off, begin data capture and drive mechanism activity, select a targeted field of view position, etc., to the control processor (456). The ultrasound mainframe (450) preferably comprises a conventional standalone ultrasound device, such as those sold under the tradenames Aspen™, Sequoia™, and Cypress™ by Siemens AG of Germany, and may be configured to communicate image data to the image processor (458) in one or several modes. For example, in one embodiment, the ultrasound mainframe (450) receives (22) from the ultrasound transducer (not shown in FIG. 4C) and sends associated image data in video standard format to the image processor. In another embodiment, the ultrasound mainframe sends image data in both video standard format and raw image data format.

The term "raw image data" is used in reference to data output from the ultrasound mainframe (450) in digital format, generally comprising an array of ultrasound image strength datapoints within the pertinent field of view, each of the datapoints being associated with a polar coordinate reference frame as acquired and then scan converted to rectilinear frame of reference for conventional display visualization. Raw image data may be sent to the image processor organized in lines, blocks, etc., and in complete sets as associated with a single image, or a subset, as associated with a particular portion of an image file, as in the scenario wherein a particular portion of a field of view is of interest. Such data processing and scan conversion to form raw image data accessible to a particular display system from a given polar coordinate or rectilinear transducer field of view frame of reference is well known in the art of ultrasound.

Due to the image capture frequency limitations associate with conventional video standards such as NTSC, 30 frames per second, and PAL, 25 frames per second, it may be desirable to send only raw image data for high-frequency updating. In a preferred embodiment, for example, operator controls, such as a mouse or footpedal, enable toggling between video standard output format at the frequency prescribed by the pertinent standard, and output to the image processor at a higher frequency using raw image data, such as at 60, 90, or 120 frames per second or other frequencies, for example, depending upon data transmission and bus considerations between the pertinent components, as would be apparent to one skilled in the art. In one embodiment, for example, an operator may use a control (454) such as a mouse to select from an image associated with the entire pertinent field of view a portion of the field of view for high-frequency updating, after which the ultrasound mainframe (450) is configured to respond by sending only the pertinent lines of raw image data at a higher frequency to the image processor (458). The notion of selecting a subportion of a captured image volume is discussed in reference to FIGS. 6A-B and 7A-B.

The image processor may comprise a personal-computer-based hardware/software system component, or may comprise a standalone workstation, such as those sold under the tradename "4-D Cardio-Scan Freehand Workstation" by TomTec Imaging Systems GmbH of Germany. Further, the ultrasound mainframe may be incorporated into a personal-computer-based hardware/software component. In addition, various components of the processor (26) embodiment depicted in FIG. 4C may be incorporated into miniaturized hardware/software components, such as application specific integrated circuits, field programmable gate arrays, groups thereof, or the like, as would be apparent to one skilled in the art. For example, in one embodiment, both the servocontroller (452) and control processor (456) comprise small integrated circuits in communication (34) with the drive mechanism (not shown in FIG. 4C) and other components.

Summarizing one preferred functionality of the system embodiment depicted in FIG. 4B, the processor (26) and associated controls hardware and software (not shown) is utilized to rotatably drive (302) the ultrasound transducer (16) field of view (242) through a selected target volume (14) with a rotational pattern sufficient to capture images of the targeted objects (224, 10, 12) during resting periods, as monitored with the associated biological signal sensor (32). For example, in the case of monitoring the position of endocardial tissue (10, 12) relative to a medical instrument (224) positioned in the heart, an EKG-sensing biological signal sensor (32) may be utilized with the control system to properly position and reposition the ultrasound transducer (16), or "gate" the ultrasound transducer (16) to the cardiac rest periods, as would be known to one skilled in the art.

Should the targeted tissue walls (10, 12) comprise the right and left atrium walls, for example, in a human wherein the average distance from the right atrium wall (10) to the far end of the left atrium (12) is about 10 centimeters, using 50 ultrasound lines and the conventional ultrasound relationship of 13 microseconds per roundtrip centimeter with the ultrasound transducer (16) positioned centrally, ultrasound images may be sampled at about 154 frames per second, or about 150 Hz per slice. Using this calculated value and a scenario wherein 10 rotationally-oriented two-dimensional slices are desired to form a relatively detailed image volume for each acquisition cycle, each image volume is acquired at a sampling frequency of about 15 Hz, preferably subject to pauses for gating around the relatively high-motion systolic heart cycle periods. Should the targeted tissue walls (10, 12) comprise walls of the left atrium, distances of 5 centimeters or less may be sampled at approximately twice these calculated rates (using 5 centimeters per ultrasound line as opposed to 10 centimeters per ultrasound line). Further, very high resolution images may be acquired, say 100 lines as opposed to 50, and 40 rotationally-oriented two-dimensional slices as opposed to 10, at approximately 1.9 Hz, and the sampling rate for each slice will still be approximately 77 Hz (frequency=1/time=1/[10 centimeter-deep slice*$13 \times 10^{-6}$ round trip speed of sound*100 lines]), which is significantly faster than the 30 Hz rate of the NTSC video standard or the 25 Hz rate of the PAL video standard, and has much higher resolution than presented with these video standards. The use of raw ultrasound data versus video standards in various embodiments of the present invention are described in further detail below in reference to FIG. 4C.

In another example wherein a high resolution is preferred and slice data is acquired at a rate of about 60 ultrasound slices per second utilizing a system such as those sold by Siemens Corporation, 30 two-dimensional slices of a targeted volume may be acquired within 500 milliseconds at the center of the resting period between healthy human heart cycles (30 slices=0.5 seconds*60 slices/second), at various rotational positions about the rotational axis of the structure to which the ultrasound transducer is coupled. In a preferred embodiment, a rotational drive mechanism such as those available from TomTec Imaging Systems GmgH may be configured to rotate an ultrasound transducer such as that featured on the product sold under the tradename AcuNav™ by Siemens Corporation at a rate sufficient to achieve approximately 2 degrees of rotational angular separation between each of the 30 adjacent slices, providing an overall image volume rotational field of view spanning approximately 60 rotational degrees (60=2 degrees between each slice*30 slices). Such a system preferably is also configured to return the transducer to a starting point during the remainder of the heart cycle to be ready to acquire 30 more slices at similar rotational positions during a subsequent heart cycle resting period. Embodiments such as those described in reference to FIGS. 4A-4C are useful for not only examining tissue structures such as the walls of a heart chamber or distal tips of medical devices, but also for examining pathology and related tissue structure behavior, such as the relationships between infarcted regions of left ventricular myocardium and chamber dynamics such as injection fraction.

Referring back to FIGS. 3A and 3B, in one embodiment, the field of view repositioning motion (302) may be paused or interrupted during acquisition of each image, while in another embodiment the repositioning motion may be continued during acquisition of the images. In a scenario wherein the targeted object volume to be imaged does not completely surround the ultrasound transducer, it may be preferable to rotate the field of view from a first position (228) imaging the first portion of the targeted object volume through to a fourth position (234) imaging the last portion of the targeted object volume and then reposition back to the first position (228) by rotating the field of view (242) in a reverse direction before the next acquisition cycle. Such a scenario is illustrated in FIG. 3A, wherein the targeted object volume as illustrated surrounds the longitudinal axis of the medical device (220) by about 120 degrees. In another embodiment, the ultrasound transducer may be rotated around in the same direction for 360 degrees with such an angular velocity that it is returned from the last position (234) back to the first position (228) before the start of a successive acquisition cycle. In another embodiment, the transducer may be rotated (302) at an angular velocity sufficient to facilitate more than one complete acquisition cycle during a single resting period between adjacent systolic heart cycles. In another embodiment, the transducer may be continuously rotated (302) throughout a single heart cycle or series of heart cycles, with blurring of the surrounding structures in images acquired during cyclic motion of the heart and slightly bowed or blurred images in the transition between each resting period and dynamic heart cycle period.

Continuing the analogy to the conventional imaging technique as depicted in FIGS. 2A-2C, FIG. 3B depicts a scenario wherein the improved technique involves four acquisition cycles (250, 252, 254, 256), each of which is positioned within a resting period, and each of which comprises successive image acquisition and repositioning from a first position (228) to a fourth position (234) before repositioning back to the first position (228) for the next successive acquisition cycle. Referring to FIG. 3C, the result is an improved ability to visualize and display three dimensional relative motion of objects within the targeted volume over time through compilation of successive image volumes (804, 806), each of which comprises images preferably acquired within the same heart cycle. A comparison (809) of a first image volume (804) comprising four two-dimensional images from a first acquisition cycle (250) to a second image volume (806) comprising four two-dimensional images from a second acquisition cycle (252), and so on for additional acquisition cycles (254, 256, etc), facilitates an improved ability to visualize changes in a displayed image volume due to the fact that the accuracy of representation of the relative position of objects within each image volume is not dependent upon homogeneity of heart cycles or acquisition cycle gating across many heart cycles. Using this technique, errors introduced by gluing many two-dimensional images together into one three-dimensional image in the presence of other out-of-cycle motion, such as breathing motion in the presence of heart motion, are eliminated, and an observer is provided with images representative of the relative positioning of objects, such as medical instruments and tissue masses, versus time. In comparison to the conventional techniques described in reference to FIGS. 2A-2C, wherein images are glued together from several moments in time and may be substantially useless for observing or guiding objects within a body in near real time, the inventive techniques provide three-dimensional relative positioning visualization based upon series of actually-acquired images, displayed in near real time. The term "near real time" is used in reference to the displaying images on a real-time pace but slightly behind actual real time due to the time associated with acquiring, processing, and displaying images using computerized hardware and software. Using a system with a processor (26) such as that depicted in FIG. 4C, near real time visualization with a time shift of less than about one second, or about one heart cycle, may be achieved. As would be apparent to one skilled in the art, subsequent to acquisition and processing, digital video or images may be controllably displayed at rates faster or slower than actual real time, or even in reverse, using conventional signal processing techniques. Further, to decrease the pitch of the image slices comprising a given image volume before displaying aspects of the image volume, additional intermediate slices may be created and added by interpolation or averaging values between adjacent actual slices.

Figure 5B:
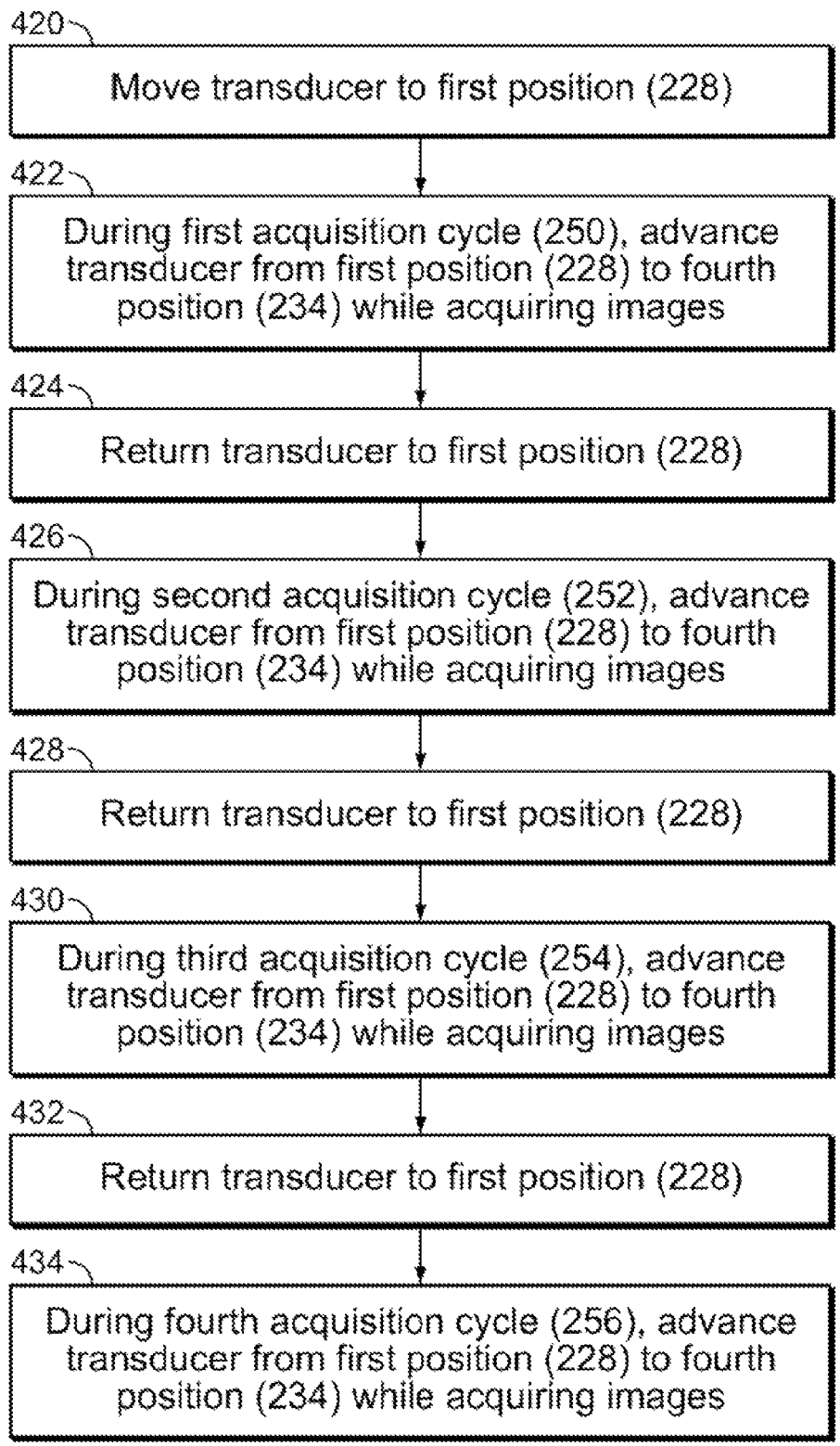
FIG. 5B depicts a flow chart representation of one embodiment of the present-invention.

Referring to FIGS. 5A and 5B, differences between a conventional technique and an embodiment of the inventive technique are highlighted in flowchart format. As shown in FIG. 5A, a conventional technique involves moving a transducer field of view to a first position (400), acquiring multiple images at that position during various points in time during a resting period (402), then moving the transducer field of view to a second position (404), acquiring multiple images at that position during various points in time during a resting period (406), moving the transducer field of view to a third position (408), acquiring multiple images at that position during various points in time during a resting period (410), moving the transducer field of view to a fourth position (412), and acquiring multiple images at that position during various points in time during a resting period (414), after which the acquired images may be "glued together" as described above in reference to FIGS. 2A-2C to facilitate visualization of the relative positions of objects in the target volume over time.

Referring to FIG. 5B, one embodiment of the inventive technique comprises moving a transducer field of view to a first position (420), acquiring a first series of images as the field of view is advanced from the first position through to the fourth position (422), then returning the transducer back to the first position (424) for successive similar cycles (426, 428, 430, 432, 434).

In another embodiment, each image volume may be acquired over two or move heart cycles. For example, in the case of a relatively large target object volume, it may be desirable to acquire a first half or third of an image volume during a first resting period utilizing the aforementioned technique of repositioning between acquisition of each image, followed by a pause in repositioning and acquisition during a systolic heart cycle, and continuation through the second half or third of the image volume acquisition during a subsequent resting period, and so on. To reduce errors associated with spreading an image volume across too many different heart cycles, as discussed above in reference to conventional techniques, it is preferable to acquire the entire image volume during adjacent resting periods, and even more preferably in as few adjacent resting periods as possible. As noted above, repositioning and image acquisition preferably are paused during systolic cycles between resting periods—but in one embodiment, repositioning and image acquisition may be continued during systolic cycles resulting in some image artifact that may be removed with conventional image processing techniques or simply ignored, subject to the aforementioned preference that the acquisition of the image volume is continued after the systolic cycle during the next available successive resting period to improve accuracy.

In one embodiment, for example, a first half of a first image volume is acquired during a first resting period, and a second half of the first image volume is acquired in a second resting period to complete acquisition of the first image volume. Then the first half of a second image volume is acquired during a third resting period, followed by completion of acquisition of the second image volume during a fourth resting period. The first and second completed image volumes may then be compared, as discussed in reference to FIG. 3C, to facilitate visualization of differences in relative positions of objects within the targeted object volumes.

In another embodiment, a simplified system such as that depicted in FIG. 4A may be utilized to continuously gather images at a given frequency as the ultrasound transducer (16) is continuously repositioned (302) at a substantially constant angular velocity without pausing and repositioning to a given start point. Images acquired during the relatively high activity of systolic heart cycles present as distortion in processed and displayed images, but the relative positioning between, for example, a medical instrument (224) and a tissue wall (10, 12), for guidance and operative purposes is presented accurately in between the distorted images—with a relatively simple system configuration.

Figure 6B:
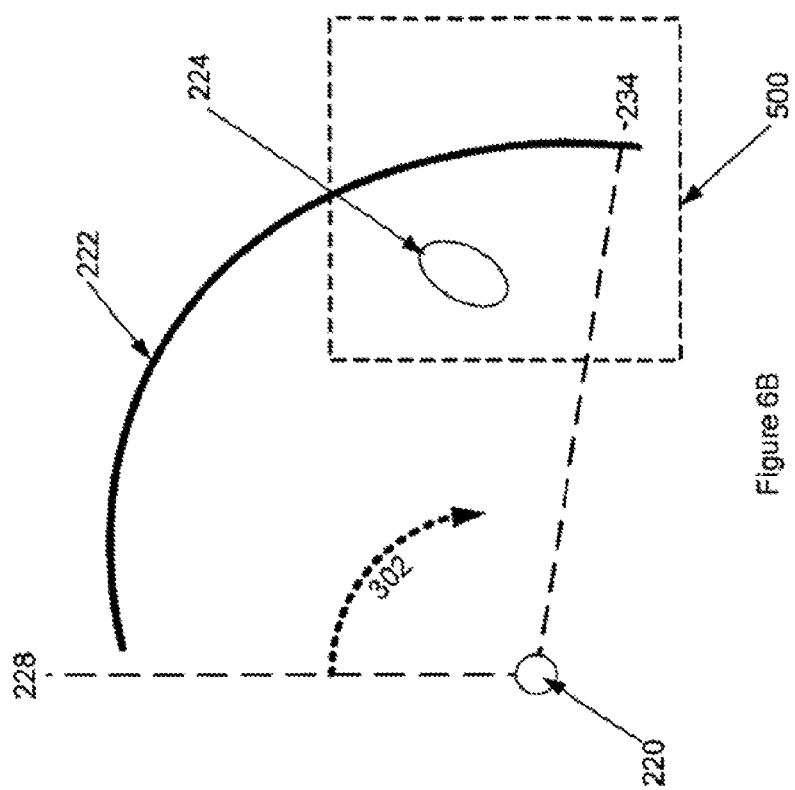
FIG. 6B depicts a cross-sectional slice of subject tissue mass and medical instrument represented with image distortion.
Figure 6A:
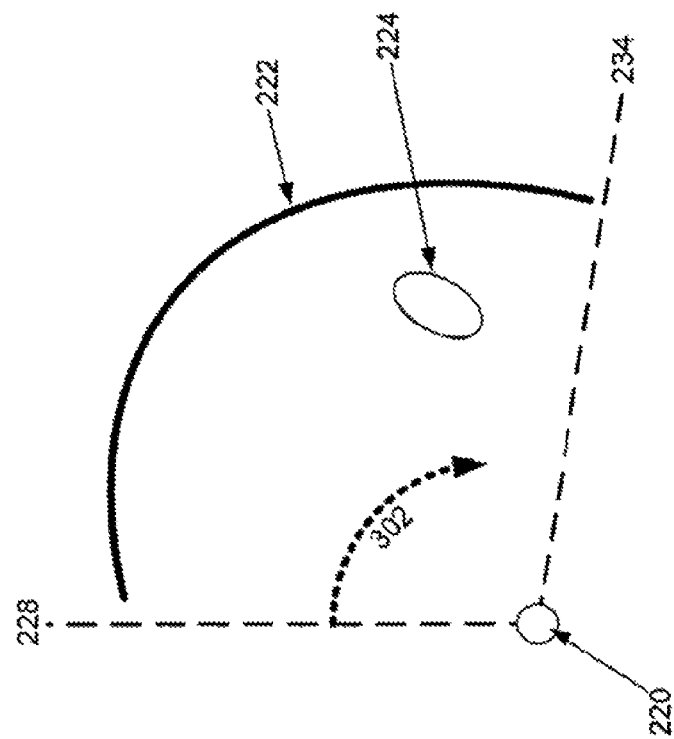
FIG. 6A depicts a cross-sectional slice of subject tissue mass and medical instrument represented without image distortion.

Referring to FIG. 6A, a targeted object volume may contain a significant amount of unneeded data for purposes of observing the relative positioning between two objects, such as a medical device (224) and a tissue wall (222). It may be desirable, therefore, to acquire and display changes in a large image volume, and then also allow a user to focus updating of the image volume upon a smaller, more concentrated image volume—preferably one focused upon the object volume regions closest (500) to the relative positioning of the two objects of interest (224, 222), as depicted in FIG. 6B. Such "zooming-in" may be accomplished by "cropping" each image dataset, or limiting the data comprising each image which is sent to the display system (28). Image cropping may be complemented or improved by modifying gain and transducer transmission focus utilizing well known ultrasound relationships. For example, if a rotating ultrasound transducer (220) is configured to rotate through a field of view of approximately 100 degrees, as depicted in FIG. 6B, with a transducer gain and transmitter focus configured to capture image data from directly adjacent the transducer (200) to a position well beyond the farthest object of interest, there is an opportunity to modify gain and transducer transmission focus for optimized performance with a more concentrated image volume (500), and also crop the acquired datasets to focus on the concentrated image volume (500) without updating, compiling, and displaying to the full extent of the system as positioned.

Figure 7A:
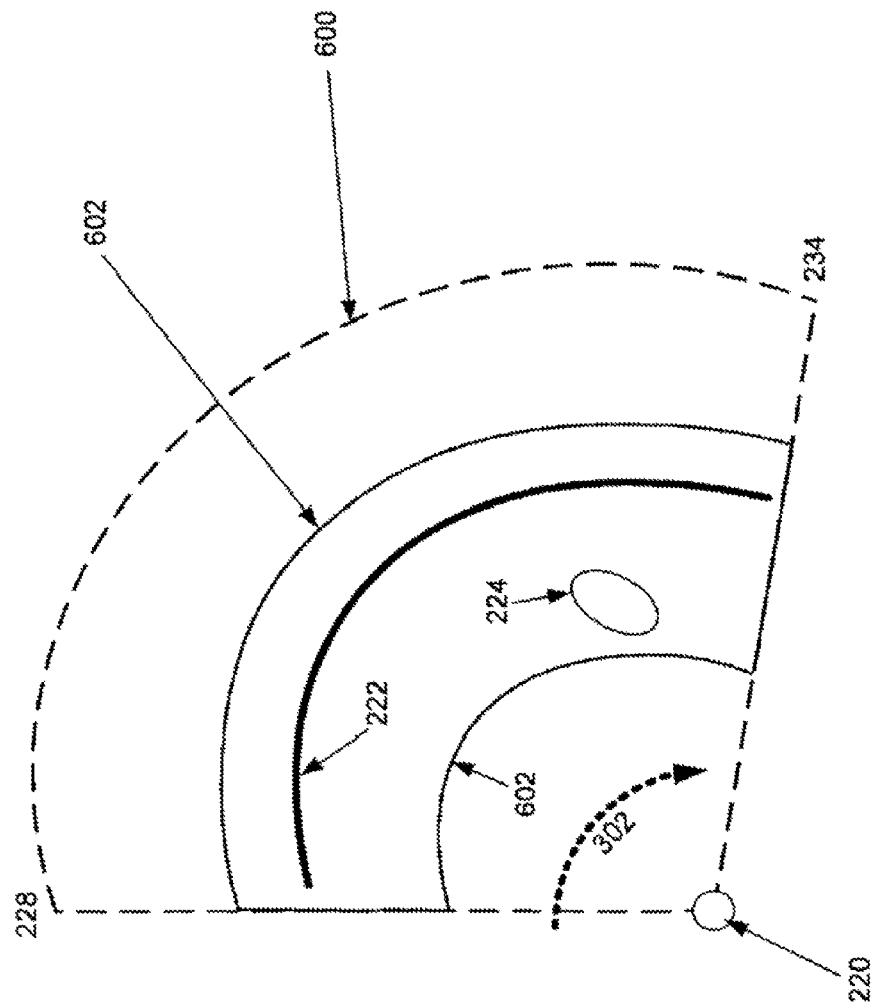
FIG. 7A depicts a top view of field of view paths of subject tissue mass and medical instrument wherein relatively large and relatively focused fields of view are illustrated.
Figure 7B:
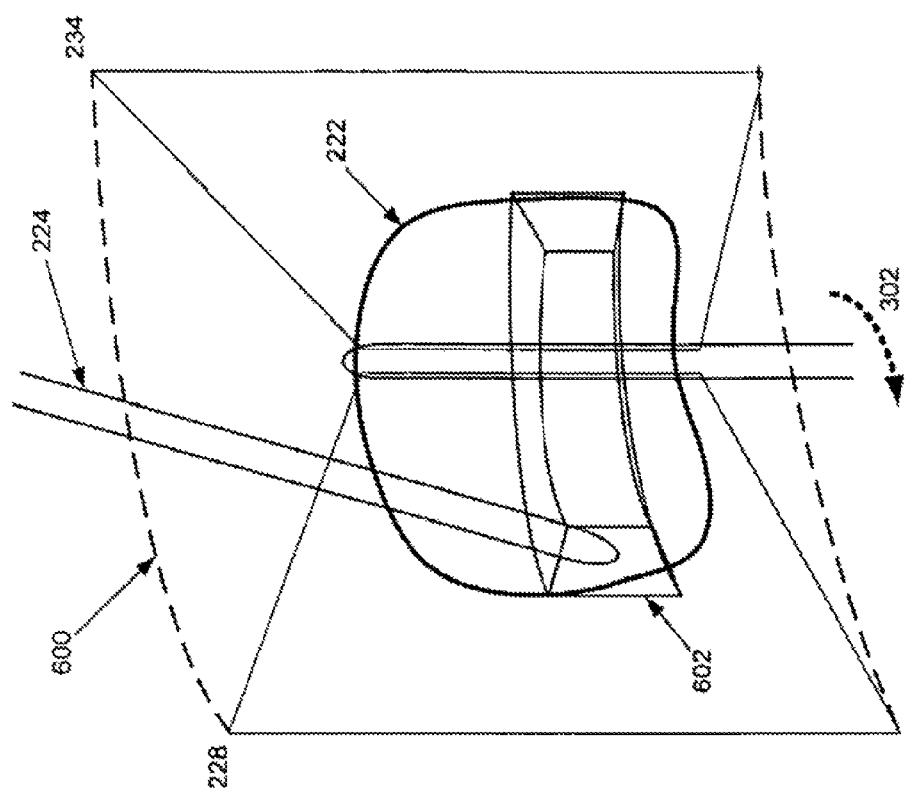
FIG. 7B depicts a side view of the objects and fields of view depicted in FIG. 7A.

FIGS. 7A and 7B depict an illustrative embodiment wherein there is a decreased need to continually acquire compile, and display differences within a larger image volume envelope (600) since a smaller, cropped image volume envelope (602) provides the requisite data for observing relative positioning between two objects (222, 224).

Figure 7C:
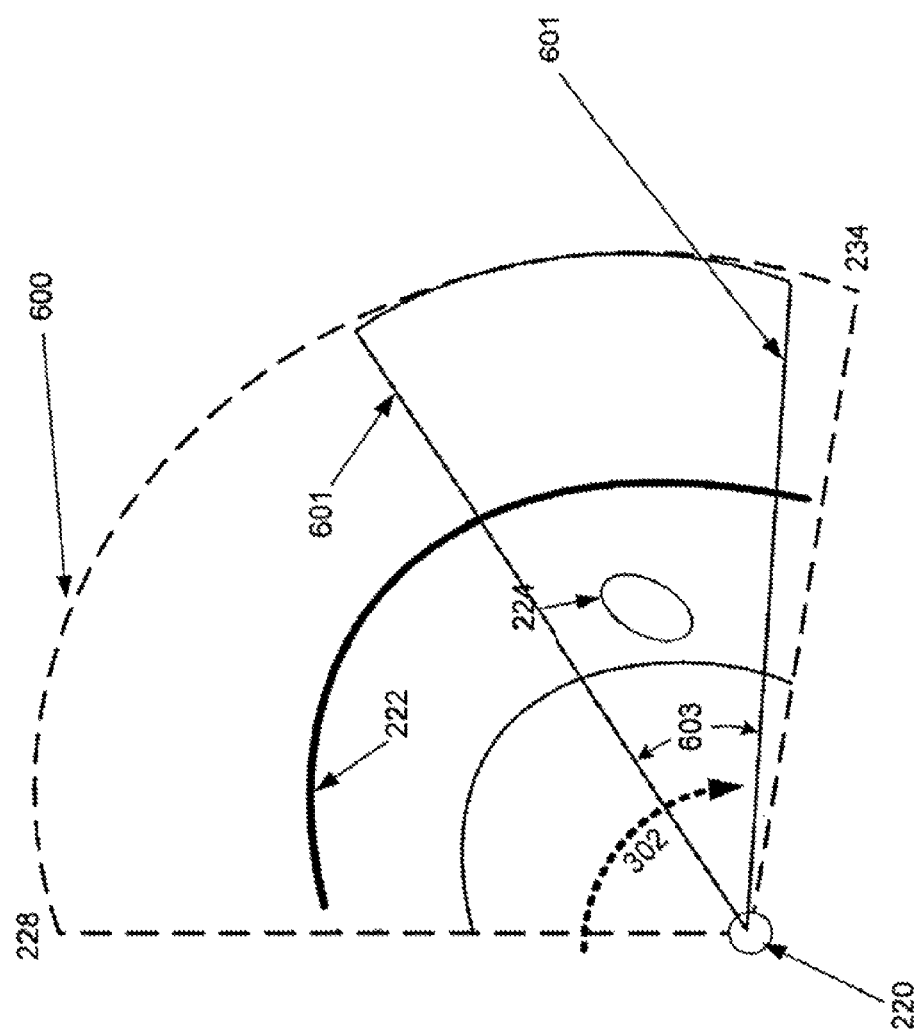
FIG. 7C depicts a top view of field of view paths of subject tissue mass and medical instrument wherein relatively large and relatively focused fields of view are illustrated.

A decreased range-of-motion may also be utilized to focus on a particular aspect of a larger image volume. For example, if after viewing a larger image volume acquired with about 180 degrees of repositioning rotation, it becomes apparent that the key area of focus, due to the position of a pertinent tissue structure or other object, is around the middle 60 degrees of the larger target volume, then the rotation and repositioning of the transducer may be focused to temporarily repeatably acquire data in the middle 60 degrees of the target volume. Referring to FIGS. 7C and 7D, embodiments illustrative of range of motion zooming-in to form a decreased volume envelope (601). As shown in FIG. 7C, an embodiment is depicted wherein range of motion zooming-in through a reduced field of view swing angle (603) causes image acquisition to be focused on a decreased volume envelope (601). FIG. 7D depicts a side view of a similar embodiment wherein a reduced field of view swing angle (603) focuses image acquisition upon a decreased volume envelope (601). At a given field of view swing angular velocity at which the transducer swings through the pertinent field of view, a decreased field of view swing angle (603) such as those depicted in FIGS. 7C and 7D generally contributes to faster cycling of the transducer through the pertinent field of view. This may be advantageous in scenarios wherein fast updating is preferred. For example, depending upon system throughput issues such as data bus and swing angular velocity, it may be difficult to gather data through a large swing angle with the limited time during a diastolic heart cycle resting period, and then conduct a repositioning swing to place the transducer in a ready position before the start of the immediately subsequent diastolic heart cycle resting period—but a reduced field of view swing angle may change this dynamic significantly, facilitating capture of an entire reduced volume envelope (601) during each diastolic resting period.

Multiple modalities of focusing or zooming-in upon a smaller image volume may be combined. For example, both range-of-motion limitation and image cropping may be utilized upon to focus upon a particular image volume and provide greater image throughput, which may facilitate higher frequency display updating, depending upon the data bus and processing limitation of the various components of the system, as would be apparent to one skilled in the art.

For example, in one preferred embodiment, the display system (28) is configured to show two images—one of a larger image associated with a larger image volume, and a second of a smaller focused image volume. Utilizing operator controls (454) such as a mouse, the operator may select a focus volume from the larger image, the focus volume being limited by range-of-motion, cropping, or both, subsequent to which the second image associated with the focused image volume is updated at relatively high frequency due to the data throughput increases associated with the smaller image volume. Should the user become disoriented or wish to toggle away from the smaller image volume back to the larger image volume, such a selection may be made with operator controls, such as a mouse, footpedal, or microphone, to return back to the original image updating frequency for the larger volume, subsequent to which a similar toggling may be utilized return high frequency updating to the smaller image volume. Alternatively, the additional throughput associated with the smaller image volume may be utilized to gather images at a decreased pitch through the selected smaller image volume for enhanced image volume resolution. In another embodiment, a larger image volume may be updated at a lower frequency than an associated smaller focus image volume. For example, in such an embodiment, a first displayed image may represent an image volume "snapshot" of the larger image volume as updated every five or six heart cycles, and a second displayed image may represent a smaller image volume as updated one or more times per heart cycle in between the larger image volume snapshot cycles.

Referring to FIG. 8A, a selected smaller-sized image volume (602) is depicted encapsulating the relative positioning of a subject tissue mass (222) and a medical instrument (224). In an embodiment wherein four images (700, 702, 704, 706) are acquired from the limited image volume (602) during rotational repositioning (302) of the depicted side-firing ultrasound catheter (220), the rotational positioning (228, 230, 232, 234) of the images (700, 702, 704, 706) relative to the position of the ultrasound catheter (220) may be as depicted in FIG. 8B. As described above, these four images may subsequently be displayed as an image volume from the perspective of the ultrasound catheter (222) using the aforementioned techniques.

Figure 8C:
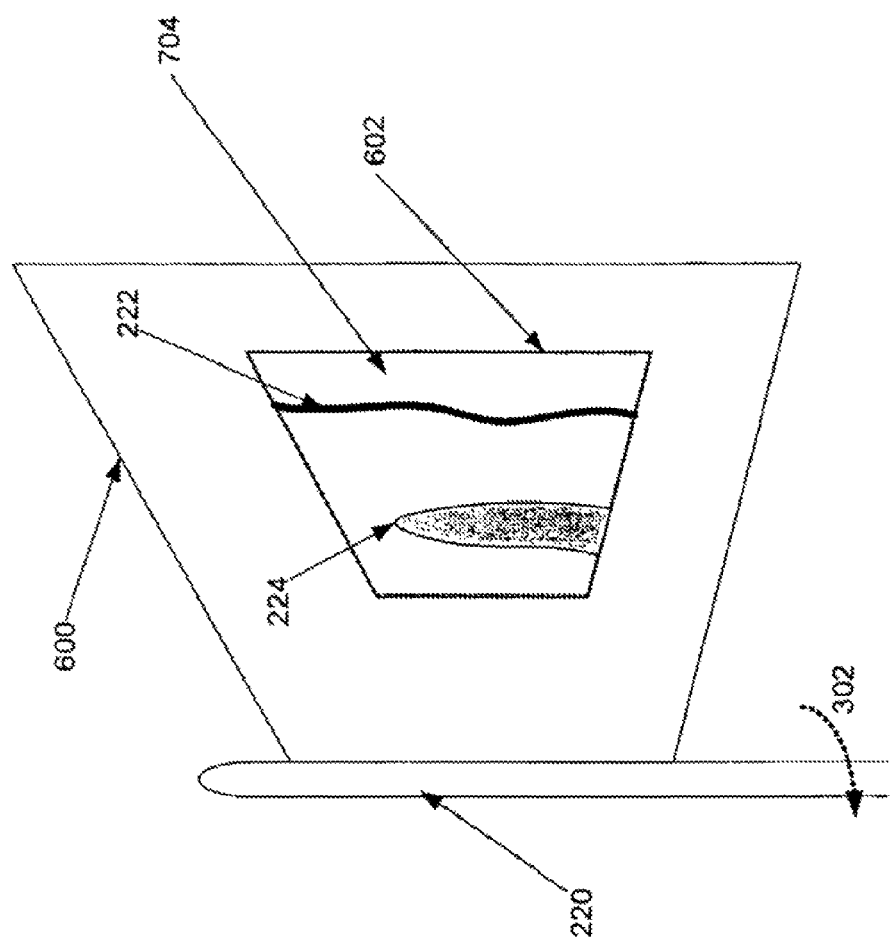
FIG. 8C depicts a side view of an image acquired utilizing the field of view path illustrated in FIG. 8A.

Alternatively, it may be useful to display the image volume from a different perspective in space—i.e., one other than the perspective as acquired from the position of the side-firing ultrasound catheter. For example, referring to FIG. 8C, a simulation of a view of one of the images (704) from FIG. 8B is depicted as viewed from a calculated perspective approximately 90 degrees orthogonal to the perspective as acquired. As shown in FIG. 8C, a view of the image data from a recalculated perspective, produced utilizing conventional techniques such as those employed in computed tomography and magnetic resonance imaging systems, is displayed in FIG. 8C in a perspective typical of those conventionally utilized with two-dimensional ultrasound devices. Depending upon the pertinent dataset underlying the image, such a view may be particularly useful for visualizing the relative positioning between the subject tissue mass (222) and the medical instrument (224). Indeed, such a perspective may be highly useful for viewing several of the four images (700, 702, 704, 706) acquired during an acquisition cycle such as that depicted in FIGS. 8A and 8B.

Figure 8D:
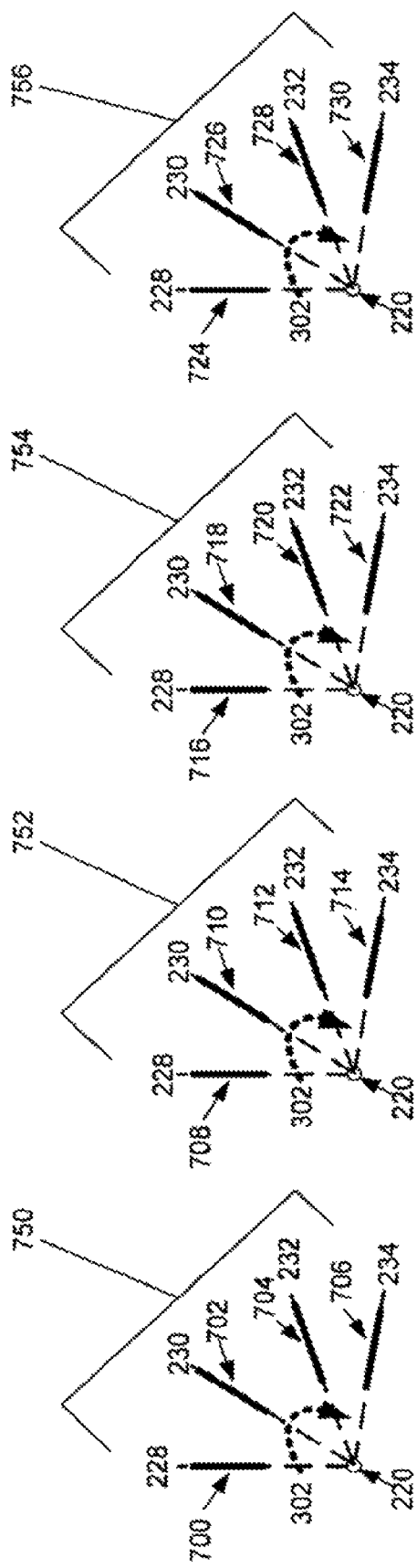
FIG. 8D depicts a top view of four sequential series of images, each having four images capturing aspects of a field of view path similar to that illustrated in FIG. 8A.

Furthermore, a recalculated perspective may be useful for visualizing the changes in a given image from one acquisition cycle to another. For example, FIG. 8D depicts four sets of four images, each set being acquired during a different acquisition cycle (750, 752, 754, 756), in an analogous fashion to those described above in reference to FIGS. 3A-3C. Perspective recalculation may be described in terms of two factors: perspective origin, and perspective vector. Referring to FIG. 8C, for example, the perspective origin, as viewed by the reader of FIG. 8C, is at the viewer's eye location above the page, while the perspective vector is from the viewer's eye into the page upon which the drawing is printed. The notions of perspective origin and perspective vector are described in further detail below in reference to FIGS. 8G and 8H. The capability to orient and dissect a three-dimensional orientation of images to visualize structures of interest in manners not available by viewing one of the acquired two-dimensional images can be significantly advantageous.

Figure 8F:
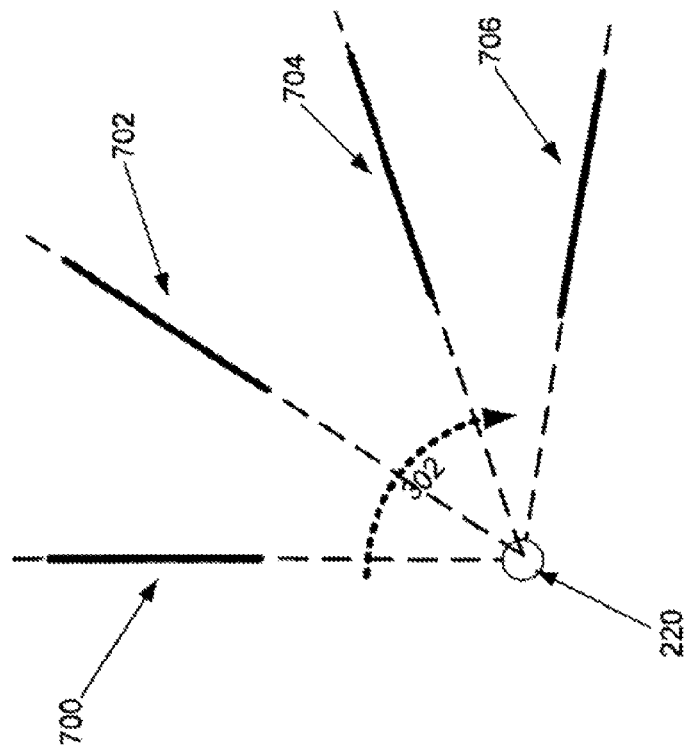
FIG. 8F depicts four images in a series oriented as acquired, as in FIG. 8B.
Figure 8E:
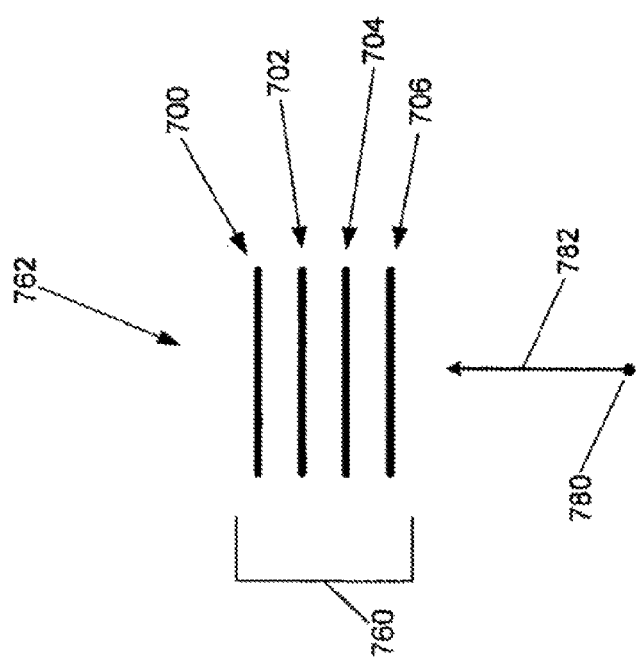
FIG. 8E depicts an image stack or image volume orientation of images acquired as illustrated, for example, in FIG. 8B.

In addition to perspective recalculation, image alignment within each series or recalculated series may be useful for observing relative positioning of objects within a given image volume. For example, it may be preferable to realign or reorient each of the images in a given series with or without perspective recalculation. Referring to FIG. 8E, for example, each of the four images (700, 702, 704, 706) naturally oriented per the acquisition perspective as depicted in FIG. 8B, 8D, or 8F has been reoriented to form an image stack (760) having a volumetric shape (762) roughly equivalent to that of a rectangular prism. This volumetric shape (762) may be preferred, for example, in a scenario wherein the observer desires to see if there is any contact between a medical instrument (224) and a tissue mass (222) from a perspective origin (780) and perspective vector (782) as depicted in FIG. 8E.

In one embodiment of the inventive system, perspective origin and perspective vector may be selected by the user using operator controls. For example, in one embodiment, a mouse or other pointing device is utilized by the user to position a dot representing a perspective origin location superimposed upon an updated image volume, and to drag the mouse or pointing device to select the perspective vector associated with the particular perspective origin, while a recalculated view of the updated image volume is displayed adjacently in another display frame in accordance with the selected perspective origin and vector. Tools and software for recalculating and presenting perspective views based upon selected perspective parameters are well known in the art of image processing, and are commonly featured in software applications such as the one sold under the tradename "Solidworks™" by Solidworks Corporation.

In another embodiment, perspective origin, perspective vector, and image orientation may be selected using controls similar to those described above, with the addition of image orientation selectability. In one embodiment, for example, a user is able to selectably toggle between a rectangularly stacked orientation, as in the illustration of FIG. 8E, and an oriented as acquired orientation, as in the illustration of FIG. 8F, using a graphical user interface, as updated images of an image volume in an adjacent viewing window are modified accordingly.

Figure 8G:
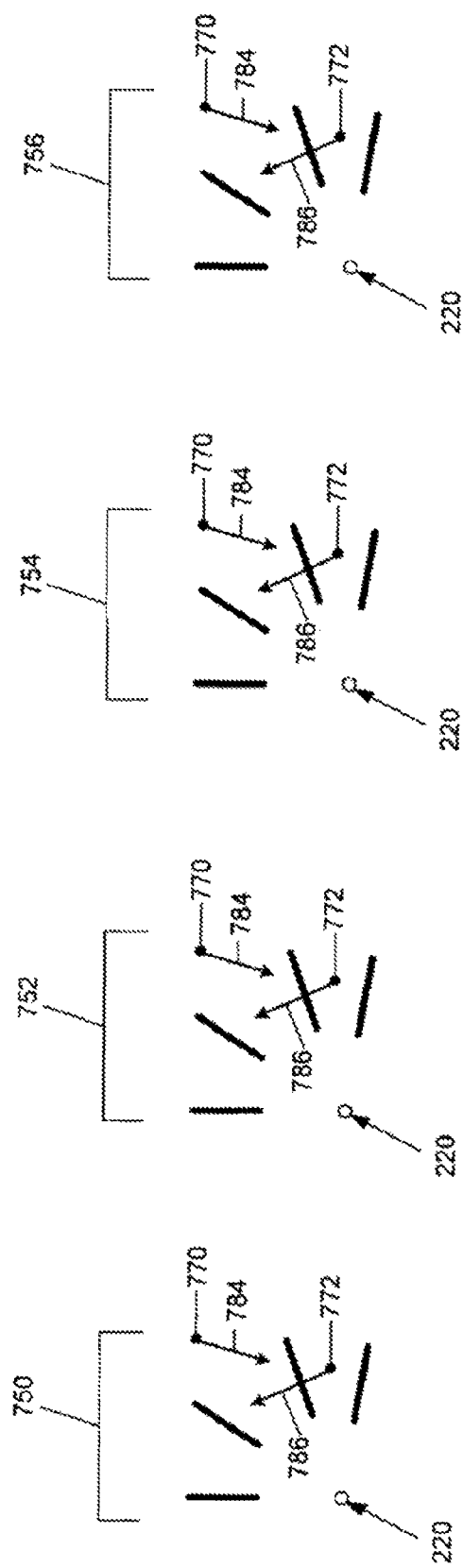
FIG. 8G depicts four sets of four images, each being oriented as acquired.
Figure 8H:
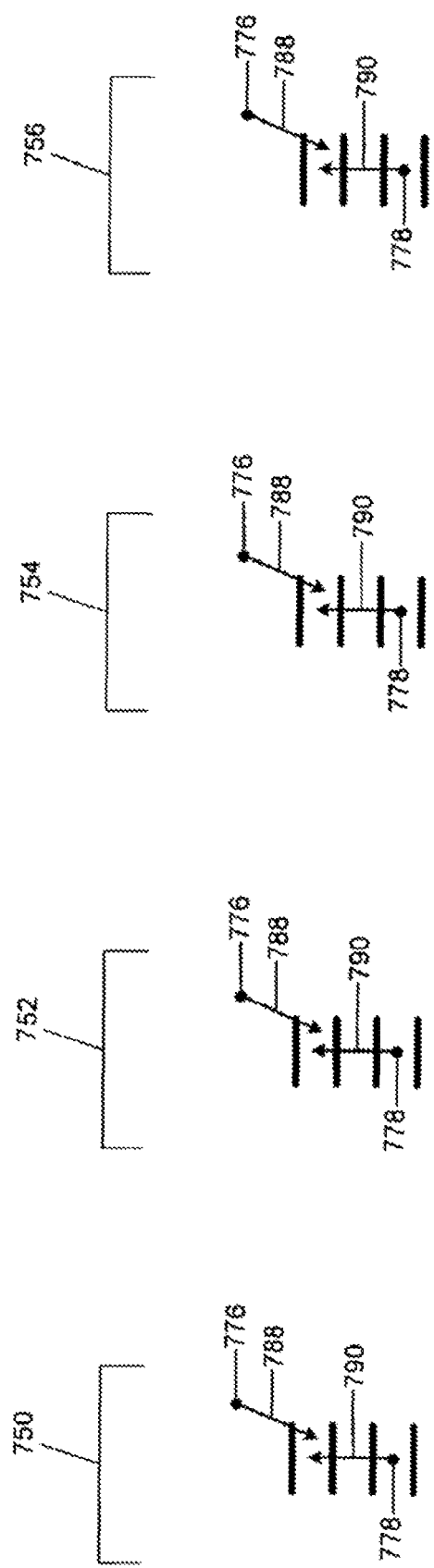
FIG. 8H depicts four sets of four images, each being reoriented into a rectangular image stack.

Referring to FIGS. 8G and 8H, four sets of four images are depicted in different orientations with various perspective origins and perspective vectors for illustrative purposes. Referring to FIG. 8G, each of the images in each of the four series (750, 752, 754, 756) is oriented as acquired about an ultrasound catheter (220). Two different perspective origins (770, 772) are depicted, each with a different perspective vector (784, 786). One of the depicted perspectives (772, 786)), for example, effectively places the viewer within the image stack looking into the third acquired image in the stack toward the second. With the other depicted perspective (770, 784), the viewer is effectively placed outside of the image stack looking into the third acquired image toward the fourth. As would be apparent to one skilled in the art, the selectability of perspective origin and perspective vector gives an operator innumerable potentially useful views of stacked image data, any one of which may be the most valued from a relative positioning or guidance perspective, depending upon the structures involved.

Referring to FIG. 8H, four sets (750, 752, 754, 756) of four images are depicted in an analogous fashion to those of FIG. 8G, with the exception that the images acquired within each acquisition cycle have been reoriented to a rectangularly stacked orientation similar to that described in reference to FIG. 8E. Two different perspective origins (776, 778), each with a different perspective vector (788, 790), are depicted for illustrative purposes. As shown in FIG. 8H, one of the perspectives (776, 788) effectively places the viewer outside of the rectangularly-oriented image stack looking diagonally at an orthogonal view of the stack toward the first acquired image of the stack. The other illustrated perspective (778, 790) effectively places the viewer inside of the image stack looking toward the third acquired image straight through second and first acquired images in the stack.

In another embodiment, two related but slightly different perspectives may be calculated and presented for a three-dimensional display effect. Referring to FIG. 9A an image stack is depicted with two different but related perspectives. Each of the images in the series of FIG. 9A is oriented as acquired about an ultrasound catheter (220). Two converging perspective vectors (54, 56) and two slightly separated perspective origins (50, 52) are utilized to calculate two perspectives—each of which is presented to a different eye of an operator using conventional three-dimensional display techniques. The spacing (58) between the perspectives is representative of the intraocular distance utilized to simulate three-dimensional perspectives using conventional hardware and techniques. For example, polarized goggles and image shuttering, color separation from one perspective to another and goggles with lenses of different color, goggles with separate displays to broadcast separate perspectives to separate eyes, "glasses-free" three-dimensional perspective monitors such as those available under the tradename "SynthaGram™" by StereoGraphics Corporation, or mirroring to direct the two eyes to separate displays, each of which broadcasts a separate perspective, such as the imaging systems available from Intuitive Surgical Corporation, all are conventional three-dimensional viewing modalities which may be incorporated into an embodiment of the inventive solution.

Figure 9B:
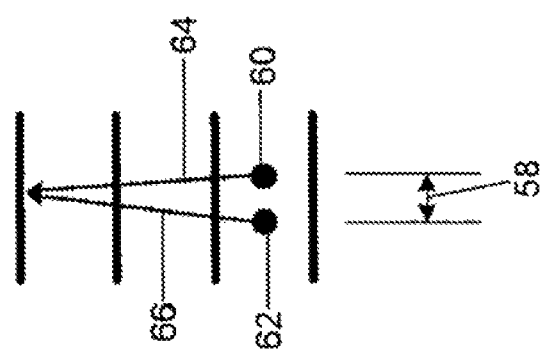
FIG. 9B depicts four images in a series reoriented into a rectangular image stack with two separate but similar viewing perspectives.
Figure 9A:
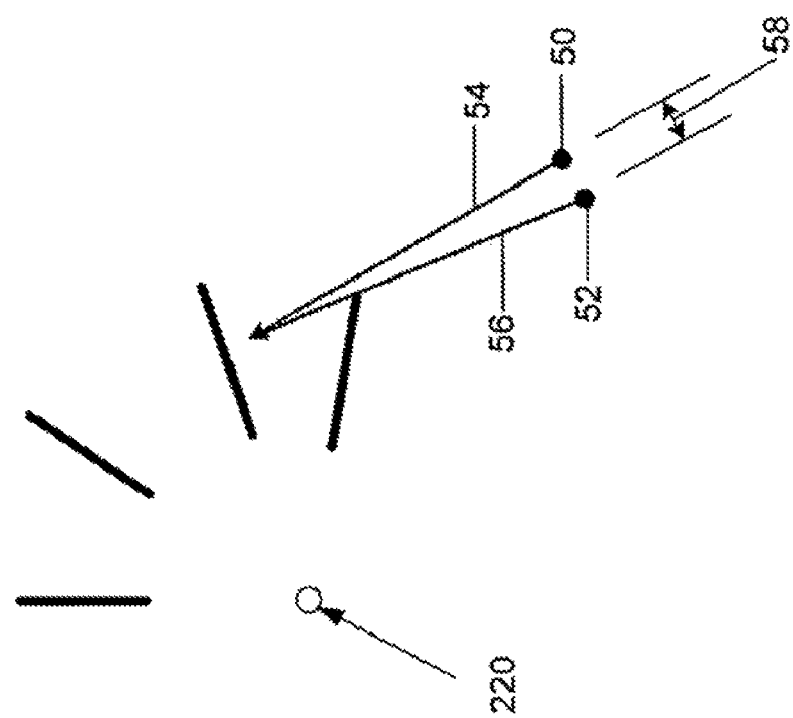
FIG. 9A depicts four images in a series oriented as acquired with two separate but similar viewing perspectives.

Referring to FIG. 9B, an embodiment analogous to that of FIG. 9A is depicted, with the exception that the image stack has been reoriented into a rectangularly stacked orientation. As with the embodiment depicted in FIG. 9A, two converving perspective vectors (64, 66) and two slightly separated perspective origins (60, 62) are utilized to calculate two perspectives—each of which is presented to a different eye of an operator using conventional three-dimensional display techniques. Similarly, the spacing (58) between the perspective origins (60, 62) is representative of the intraocular distance utilized to simulate three-dimensional perspectives using conventional hardware and techniques. In a preferred embodiment, one of the operator controls pertains to adjustability of the spacing (58) between perspectives to accommodate the variability in intraocular spacing among individual operators.

Although the invention is described herein with reference to specific embodiments, many modifications therein will readily occur to those of ordinary skill in the art. Accordingly, all such variations and modifications are included within the intended scope of the invention as defined by the following claims.

We claim:

1. A method for acquiring two-dimensional ultrasound images of a tissue for display in a three-dimensional orientation, the method comprising:
   locating an instrument in a body, the instrument having an axis and carrying a transducer;
   acquiring, with the transducer, a sequence of images of a tissue during a single physiological cycle, wherein each image of the sequence is acquired at a different rotational orientation of the transducer about the axis; and
   displaying the acquired images of the sequence as a three-dimensional, volumetric image.

2. The method of claim 1, wherein the sequence of images is acquired during a resting period of the single physiological cycle.

3. The method of claim 1, wherein the sequence of images is acquired during a single heart cycle.

4. The method of claim 1, wherein the instrument is located in a blood vessel and the sequence of images is acquired during a single heart cycle.

5. The method of claim 1, wherein the instrument is located in a heart and a sequence of images is acquired during a single heart cycle.

6. The method of claim 1, wherein the sequence of images is acquired during a single respiratory cycle.

7. A method for acquiring ultrasound images in a body, the method comprising:
   locating a first instrument in a body, the instrument having an axis and carrying a transducer; and
   acquiring, with the transducer, a first sequence of images during a single physiological cycle, wherein each image of the sequence is acquired at a different orientation of the transducer about the axis.

8. The method of claim 7, further comprising creating a three-dimensional, volumetric image from the acquired images of the sequence.

9. The method of claim 7, wherein the sequence of images is acquired during a resting period of the single physiological cycle.

10. The method of claim 7, wherein the sequence of images is acquired during a single heart cycle.

11. The method of claim 7, wherein the first instrument is located in a blood vessel and the sequence of images is acquired during a single heart, cycle.

12. The method of claim 7, wherein the first instrument is located in a heart and a sequence of images is acquired during a single heart cycle.

13. The method of claim 7, wherein the sequence of images is acquired during a single respiratory cycle.

14. The method of claim 7, wherein acquiring the sequence of images includes acquiring at least one image of a tissue and a second instrument positioned in proximity to the tissue to track the second instrument relative to the tissue.

15. The method of claim 7, wherein each image of the sequence is acquired at a different rotational orientation of the transducer about the axis.

16. The method of claim 7, further comprising acquiring, with the transducer, a second sequence of images during a single physiological cycle, wherein each image of the second sequence is acquired at a different orientation of the transducer about the axis.

17. A method for tracking an instrument relative to a tissue in a body, the method comprising:
   locating a first instrument in the body, the instrument having an axis and carrying a transducer;
   acquiring, with the transducer, a sequence of images of a target volume in the body during a single physiological cycle, wherein the target volume includes the tissue and a second instrument positioned in proximity to the tissue, wherein each image of the sequence is acquired at a different rotational orientation of the transducer about the axis;
   displaying the acquired images of the sequence as a three-dimensional, volumetric image; and
   tracking a position of the second instrument relative to the tissue via the volumetric image.

18. The method of claim 17, wherein the sequence of images is acquired during a resting period of the single physiological cycle.

19. The method of claim 17, wherein the sequence of images is acquired during a single heart cycle.

20. The method of claim 17, wherein the first instrument is located in a blood vessel and the sequence of images is acquired during a single heart cycle.

21. The method of claim 17, wherein the first instrument is located in a bean and a sequence of images is acquired during a single bean cycle.

22. The method of claim 17, wherein the sequence of images is acquired during a single respiratory cycle.

23. The method of claim 17, further comprising advancing the second instrument in an X, Y or Z coordinate position relative to the tissue.

24. The method of claim 23, further comprising tracking the second instrument in an X, Y or Z coordinate position relative to the tissue.

25. A method for acquiring ultrasound images of a tissue for display in a three-dimensional orientation, the method comprising:
   locating a first instrument in a body, the instrument having an axis and carrying a transducer;
   detecting a signal of a physiological cycle using a biological sensor; and
   acquiring, with the transducer, a sequence of images of the tissue during a single physiological cycle as monitored with the biological sensor to facilitate image acquisition in sync with the physiological cycle, wherein each image of the sequence is acquired at a different rotational orientation of the transducer about the axis.

26. The method of claim 25, wherein the sequence of images is acquired during a resting period of the single physiological cycle.

27. The method of claim 25, wherein the sequence of images is acquired during a single heart cycle.

28. The method of claim 25, wherein the first instrument is located in a blood vessel and the sequence of images is acquired during a single heart cycle.

29. The method of claim 25, wherein the first instrument is located in a heart and a sequence of images is acquired during a single heart cycle.

30. The method of claim 25, wherein the sequence of images is acquired during a single respiratory cycle.

31. The method of claim 25, wherein acquiring the sequence of images includes acquiring at least one image of the tissue and a second instrument positioned in proximity to the tissue to track the second instrument relative to the tissue.

32. The method of claim 31, further comprising tracking a position of the second instrument relative to the tissue via a three-dimensional, volumetric image created from the acquired images of the sequence.

33. The method of claim 25, further comprising displaying the acquired images of the sequence as a three-dimensional, volumetric image.

\* \* \* \* \*